US006355270B1

(12) United States Patent
Ferrari et al.

(10) Patent No.: US 6,355,270 B1
(45) Date of Patent: *Mar. 12, 2002

(54) PARTICLES FOR ORAL DELIVERY OF PEPTIDES AND PROTEINS

(75) Inventors: Mauro Ferrari, Dublin, OH (US); Peter J. Dehlinger, Palo Alto, CA (US); Francis J. Martin, San Francisco, CA (US); Carl F. Grove, Portola Valley, CA (US); David R. Friend, Menlo Park, CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/479,389

(22) Filed: Jan. 6, 2000

Related U.S. Application Data

(60) Provisional application No. 60/115,420, filed on Jan. 11, 1999, and provisional application No. 60/115,424, filed on Jan. 11, 1999.

(51) Int. Cl.[7] ........................... A61K 9/14; A61K 9/127; A61K 9/48; A61K 38/00; A01N 37/18
(52) U.S. Cl. ...................... 424/489; 424/450; 424/451; 424/185.1; 514/2; 514/21; 530/300; 530/350
(58) Field of Search ................................. 424/489, 450, 424/451, 185.1; 514/2, 21; 530/300, 350

(56) References Cited

U.S. PATENT DOCUMENTS

| | | | |
|---|---|---|---|
| 4,478,677 A | | 10/1984 | Chen et al. ................... 156/635 |
| 4,888,176 A | | 12/1989 | Langer et al. ............... 424/426 |
| 4,933,185 A | | 6/1990 | Wheatley et al. ............ 424/461 |
| 4,994,639 A | | 2/1991 | Dickinson et al. ...... 219/121.69 |
| 5,010,167 A | | 4/1991 | Ron et al. .................... 528/328 |
| 5,018,164 A | | 5/1991 | Brewer et al. ............... 372/109 |
| 5,236,551 A | | 8/1993 | Pan ............................. 156/643 |
| 5,313,043 A | | 5/1994 | Yamagishi .............. 219/121.68 |
| 5,368,430 A | | 11/1994 | Lin ............................. 414/228 |
| 5,620,708 A | * | 4/1997 | Amkraut et al. ............ 424/491 |
| 5,702,727 A | * | 12/1997 | Amkraut et al. ............ 424/491 |
| 5,968,554 A | | 10/1999 | Beiman et al. ............. 424/480 |

FOREIGN PATENT DOCUMENTS

| | | |
|---|---|---|
| WO | WO 95/24261 | 9/1995 |
| WO | WO 95/24472 | 9/1995 |
| WO | WO 95/24736 | 9/1995 |

OTHER PUBLICATIONS

Alessio Fasano, et al, Rapid Publication The Journal of Clinical Investigation, vol. 99:1158–64; Mar. 6, 1997.
Kamini Walia et al., "Purification and Characterization of Novel Toxin Produced by *Vibro cholerae* 01" Infection & Immunity, vol. 67, No. 10, 5215–5222, Oct., 1999.
Inn–Kyu Kang, et al., "In vitro blood compatibility of functional group–grafted and heparin–immobilized polyurethanes prepared by plasma glow discharge", Biomaterials, vol. 18, No. 16, pp. 1099–107, 1997.
Rajender Sipehia, "The Enhanced Attachment and Growth of Endothelial Cells on Anhydrous Ammonia Gaseous Plasma Modified Surfaces of Polystyrene and Poly (Tetrafluoroethylene)", Biomaterials, Artificial Cells and Artificial Organs, vol. 18, No. 3, pp. 437–446, 1990.
Shu Quin Liu, et al., "Cell growth on immobilized cell growth factor. 9. Covalent immobilization of insulin, transferring, and collagen to enhance growth of bovine endothelial cells", Journal of Biomedical Materials Research, vol. 27, No. 7, pp. 909–915, 1993.
Robert B. Patterson, et al., "Effects of Radiofrequency Glow Discharge and Oligopeptides on the Attachment of Human Endothelial Cells to Polyurethane", ASAIO Journal, vol. 41, No. 3, M625–M629, Nov. 13, 1995.
Inn–Kyu Kang, et al., "Preparation and surface characterization of functional group–grafted and heparin–immobilized polyurethanes by plasma glow discharge," Biomaterials, vol. 17, No. 8, pp. 841–847, Apr. 25, 1996.
Y. Ikada, "Surface modification of polymers for medical applications," Biomaterials, vol. 15, No. 10, pp. 725–736.
Christopher Bieniarz, et al., "Extended Lenth Heterobifunctional Coupling Agents for Protein Conjugations," The Biochemical Journal, vol. 7, 88–95, 1996.
Jan Carlsson, et al., "Protein Thiolation and Reversible Protein–Protein Conjugation," The Biochemical Journal, vol. 173, 723–737, 1978.
Alessio Fasano, et al., "The Exterotoxic Effect of Zonula Occludens Toxin on Rabbit Small Intestine Involves the Paracellular Pathway," Gastroenterology, vol. 112, 839–846, 1997.

(List continued on next page.)

Primary Examiner—Avis M. Davenport
(74) Attorney, Agent, or Firm—Fish & Richardson P.C.

(57) ABSTRACT

Microfabricated, asymmetrical, reservoir-containing particles for use in the oral delivery of biopolymer therapeutic agents such as peptides, proteins and oligonucleotides are disclosed. The particles are encapsulated in enteric-coated capsules or tablets to provide passage through the stomach and release of a suspension of the particles in the intestinal lumen. The particles have a selected shape, and uniform dimensions preferably in the 100 μm to 1 mm range. The reservoirs open to the face of the particle and are filled with a therapeutic agent and selected excipients. The excipients are selected to delay the dissolution/release of the agent from the particle reservoirs for 5–60 minutes after the particle is released in the intestinal lumen. Alternatively, the pore is plugged with an erodable material. The face of the particle is grafted with a layer of muco-adhesive ligands designed to quickly bind the particle to the intestinal mucosa for several minutes to several hours after release of the particles from the enteric-coated carrier.

21 Claims, 11 Drawing Sheets

OTHER PUBLICATIONS

David Y. Tseng, et al., "Effect of amide and amine plasma–treated ePTFE vascular grafts on endothelial cell lining in an artificial circulatory system," Journal of Biomedical Materials Research, vol. 42, No. 2, pp. 188–198, 1998.

Adil Denizli, et al., "Diamine–plasma treated and Cu(II)–incorporated poly(hydroxethylmethacrylate) microbeads for albumin adsorption," Journal of Biomaterials Science Polymer Edition, vol. 10, No. 3, pp. 305–318, 1998.

Nehir Ozden, et al., "Coating of silicone–based impression materials in a glow–discharge system by acrylic acid plasma," Dental Materials, vol. 13, No. 3, pp. 174–178.

Manssor Amiji, et al., "Surface modification of polymeric biomaterials with poly(ethyleneoxide), albumin, and heparin for reduced thrombogenicity", Journal of Biomaterials Science Polymer Edition, vol. 4, No. 3, pp. 217–234, 1992.

Richard F. Taylor, "Protein Immobilization Fundamentals and Applications", pp. 109110 (1991).

Alessio Fasano et al. "Zonula Occludens Toxin Modulates Tight Junctions through Protein Kinase C–dependent Action Reorganization, In Vitro", The Journal of Clinical Investigation, Inc., vol. 96, pp. 710–720, Aug. 1995.

J. P. Ballantyne, et al. "Selective Area Metallization by Electron–Beam Controlled Direct Metallic Deposition," J. Vac. Sci. Technol., vol. 1, No. 6, Nov./Dec. 1973.

Robert W. Benedict, et al. "Bonding Erythrocytes to Plastic Substrates by Glow–Discharge Activation", Biomat. Med. Dev., Art. Org., 7(4), 477–493 (1979).

L. F. Thompson, et al. "Introduction to Microlithography", Theory, Materials, and Processing, ACS Symposium Series 219, Washington, D.C. 1983.

Kalpana R. Kamath and Kinam Park, "Surface Modification of Polymeric Biomaterials by Albumin Grafting Using $\gamma$–Irradiation," Journal of Applied Biomaterials, vol. 5, pp. 163–173, 1994.

John P. Ranieri, et al. "Neuronal cell attachment to fluorinated ethylene propylene films with covalently immobilized laminin oligopeptides YIGSR and IKVAV. II," Jornal of Biomedical Materials Research, vol. 29 No. 6, Jun. 1995.

* cited by examiner

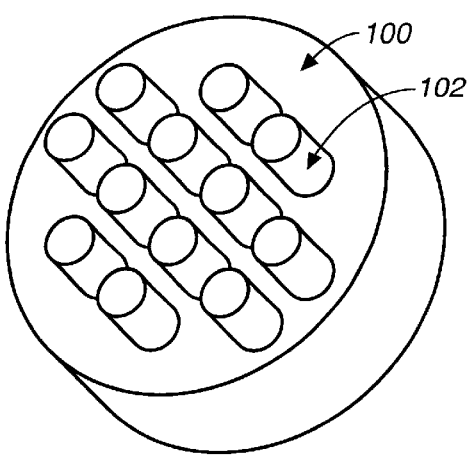
FIG._1A
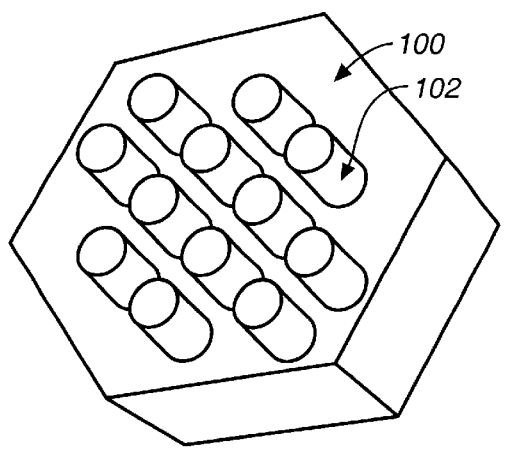
FIG._1C
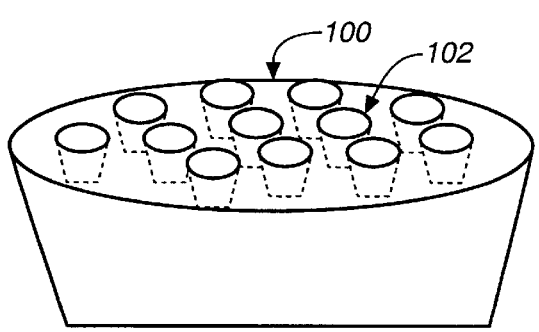
FIG._1B
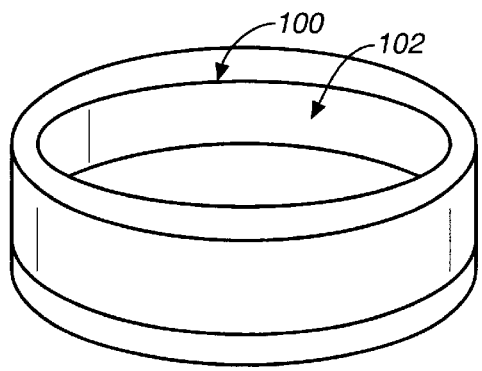
FIG._1D
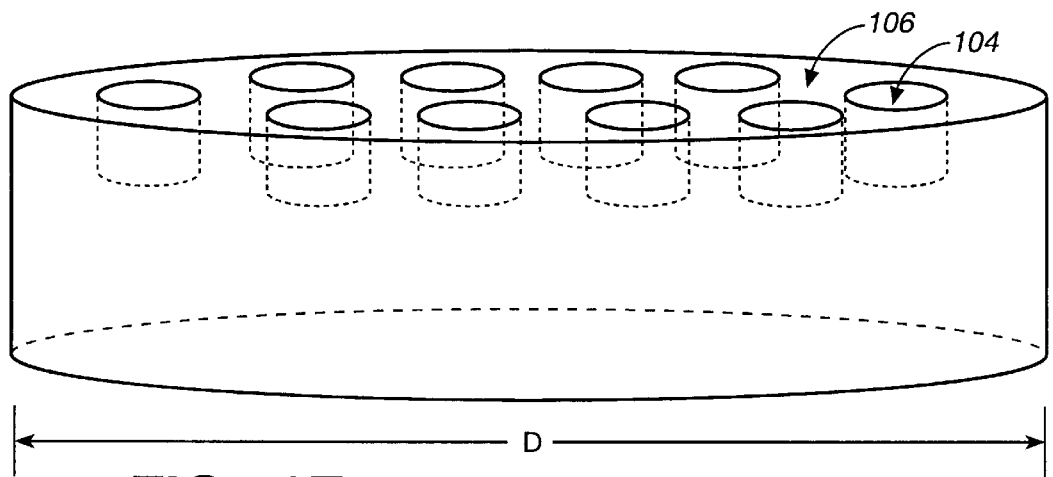
FIG._1E

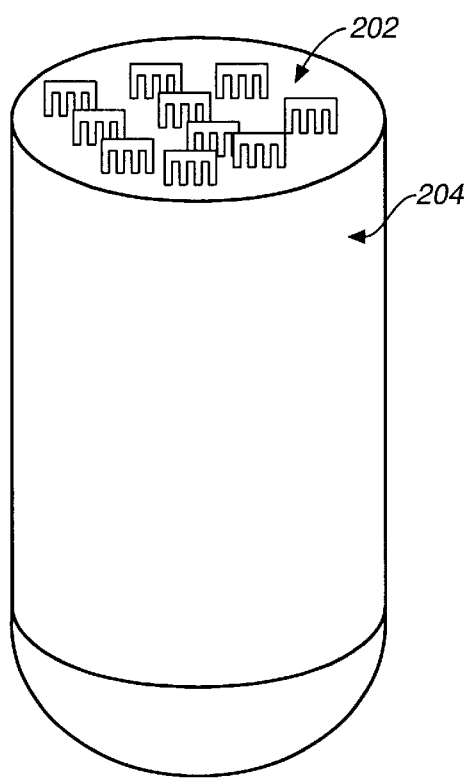
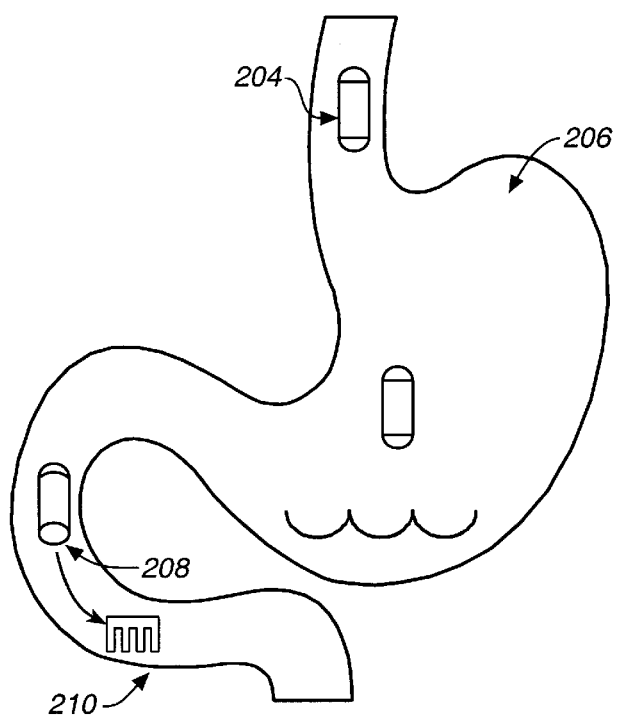
FIG._2A  FIG._2B

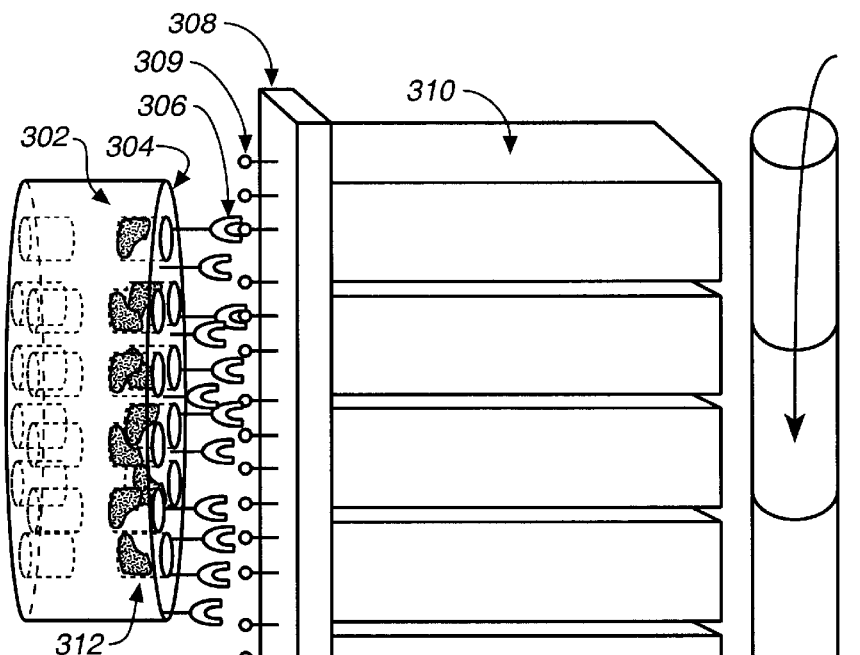
FIG._3A
1. Docking of particle, face-side to mucosal epithelium
2. Influx of water, hydration/ solvation of agent
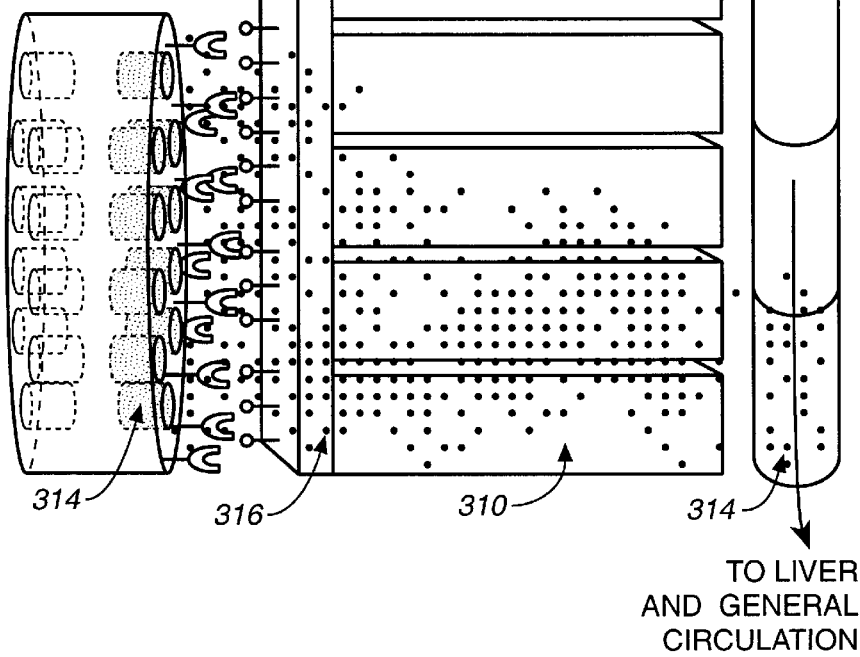
FIG._3B
3. Release of agent from reservoirs
4. Movement of agent across the intestinal epithelium
5. Entry of the agent into the hepatic portal circulation
TO LIVER AND GENERAL CIRCULATION

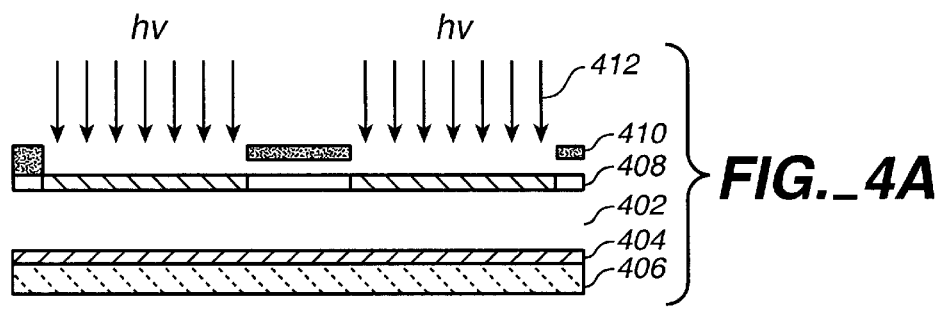
*FIG._4A*
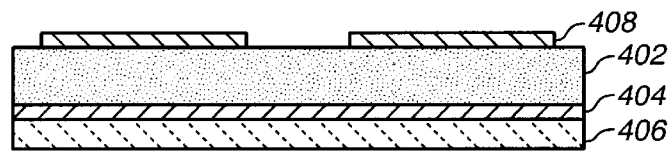
*FIG._4B*
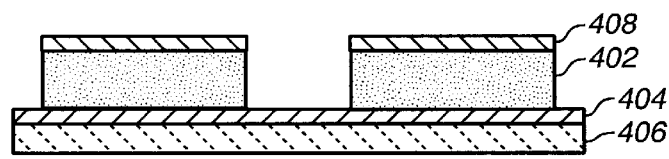
*FIG._4C*
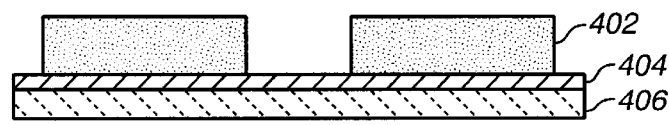
*FIG._4D*
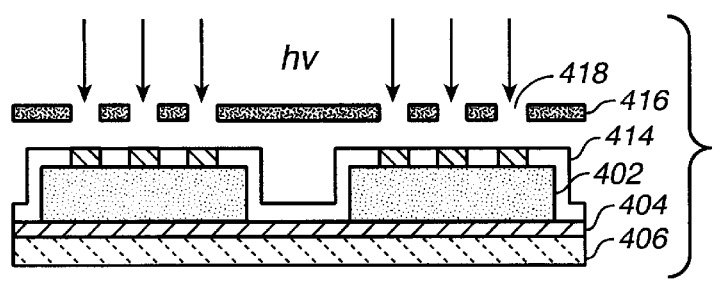
*FIG._4E*
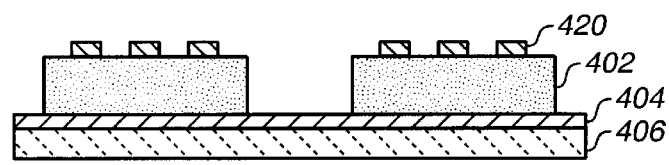
*FIG._4F*
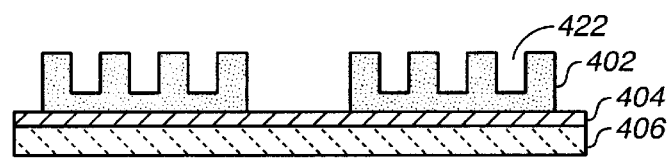
*FIG._4G*
*FIG._4H*

Polycarbonate Or Polyester Trak-Etched
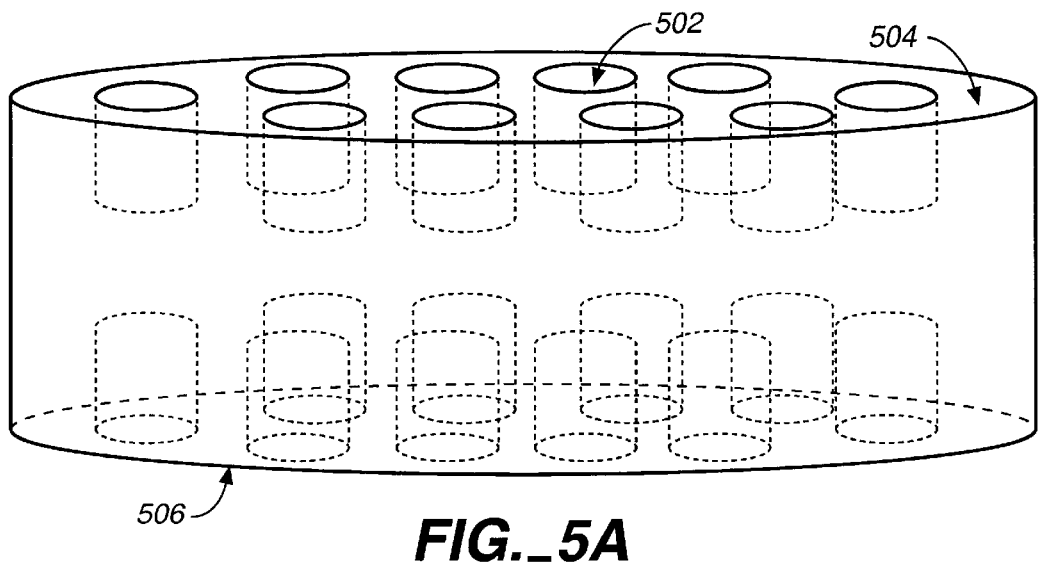
FIG._5A
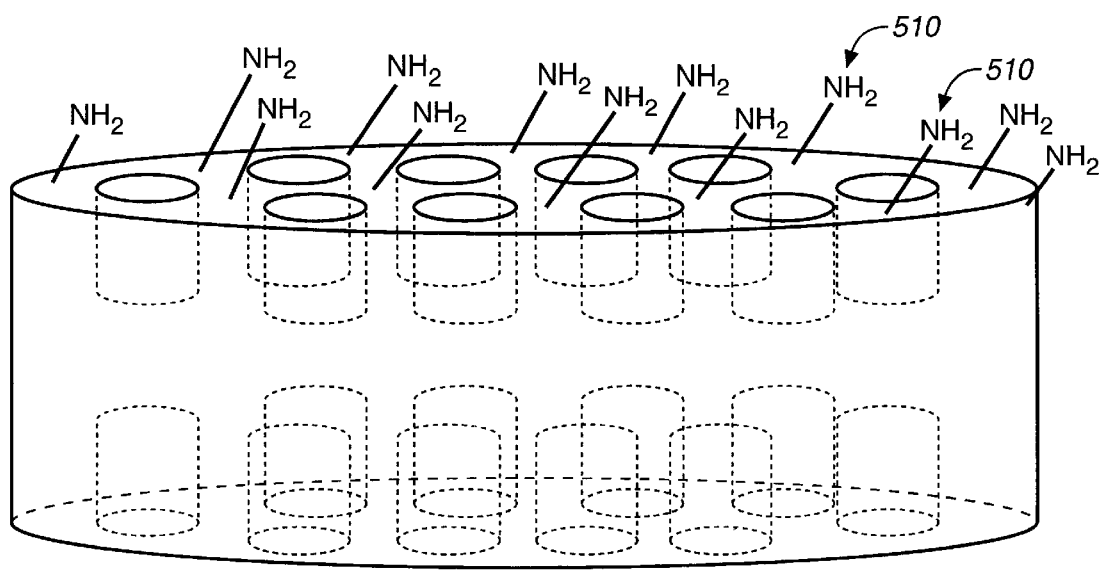
FIG._5B

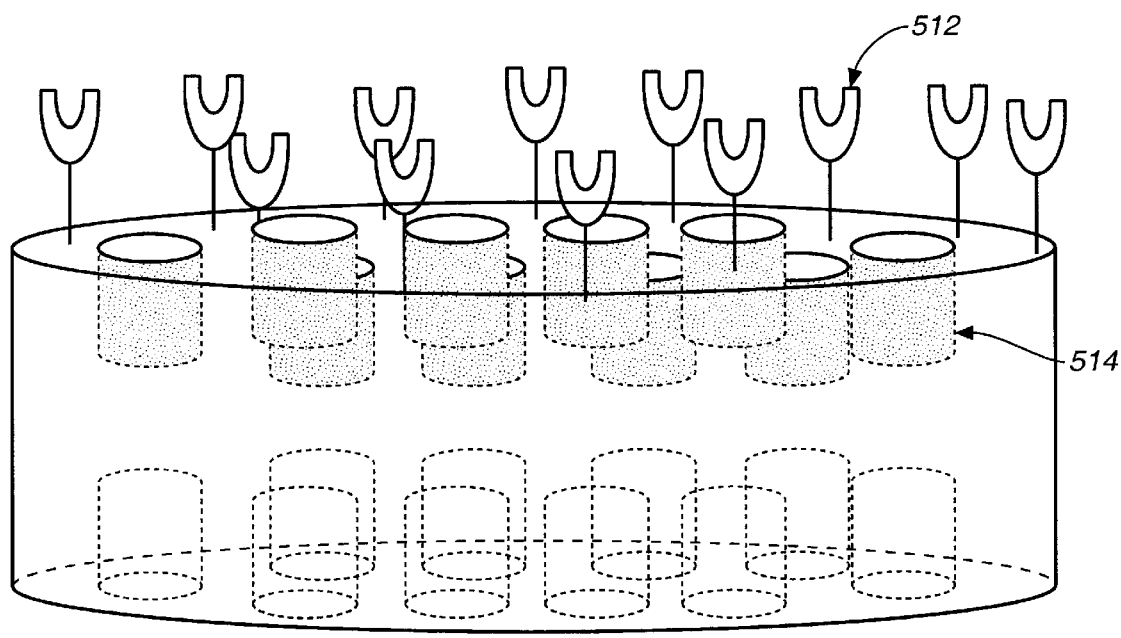
FIG._5C
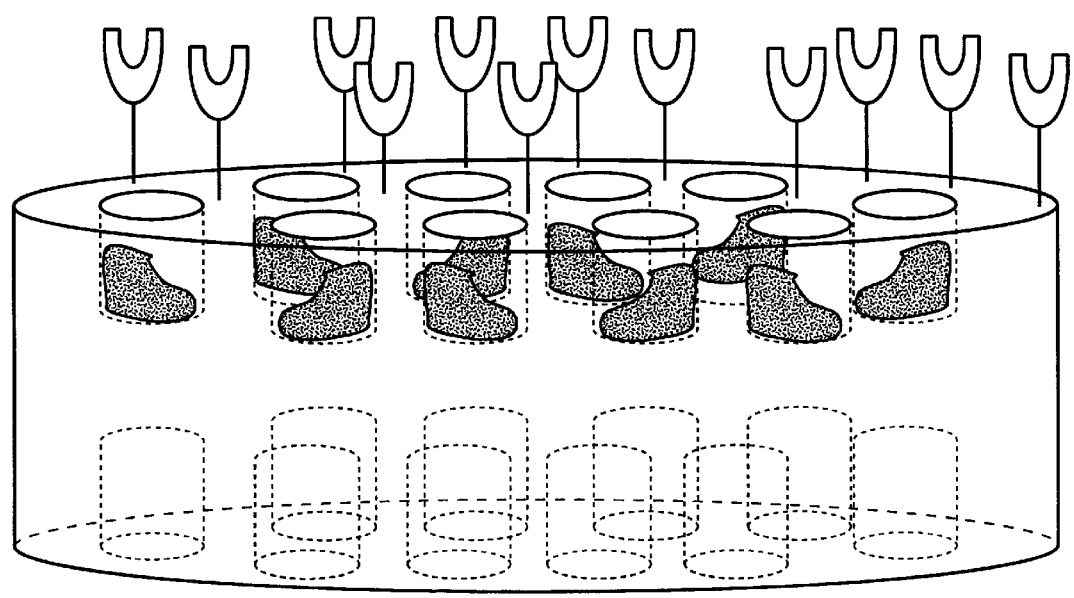
FIG._5D

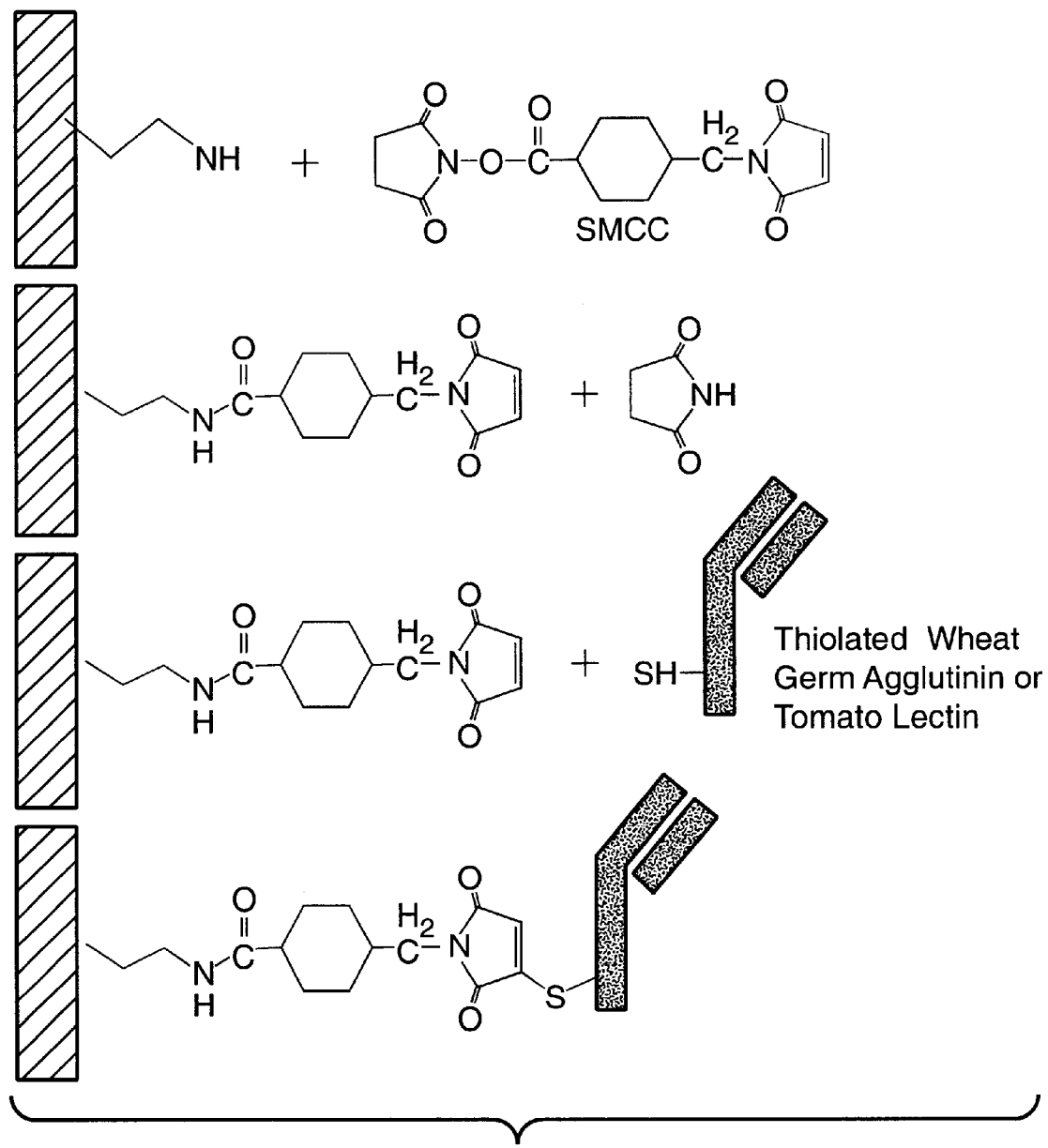
FIG._6

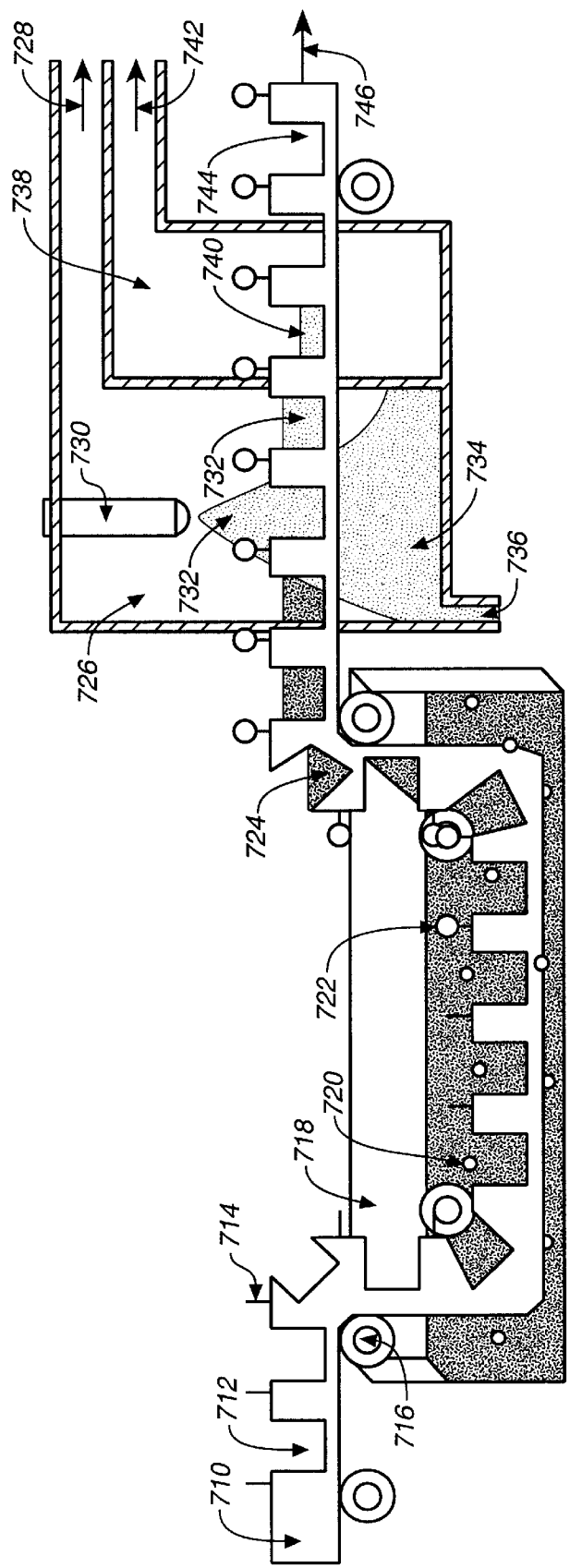
FIG._7A

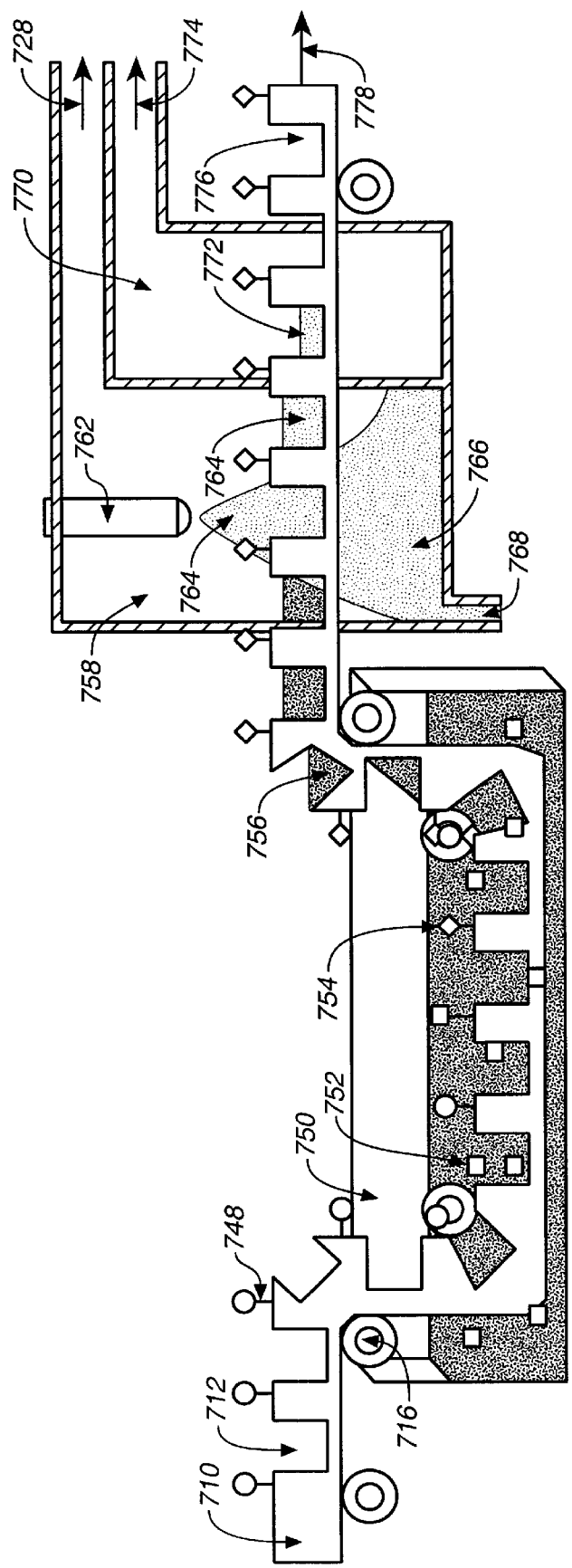
FIG._7B

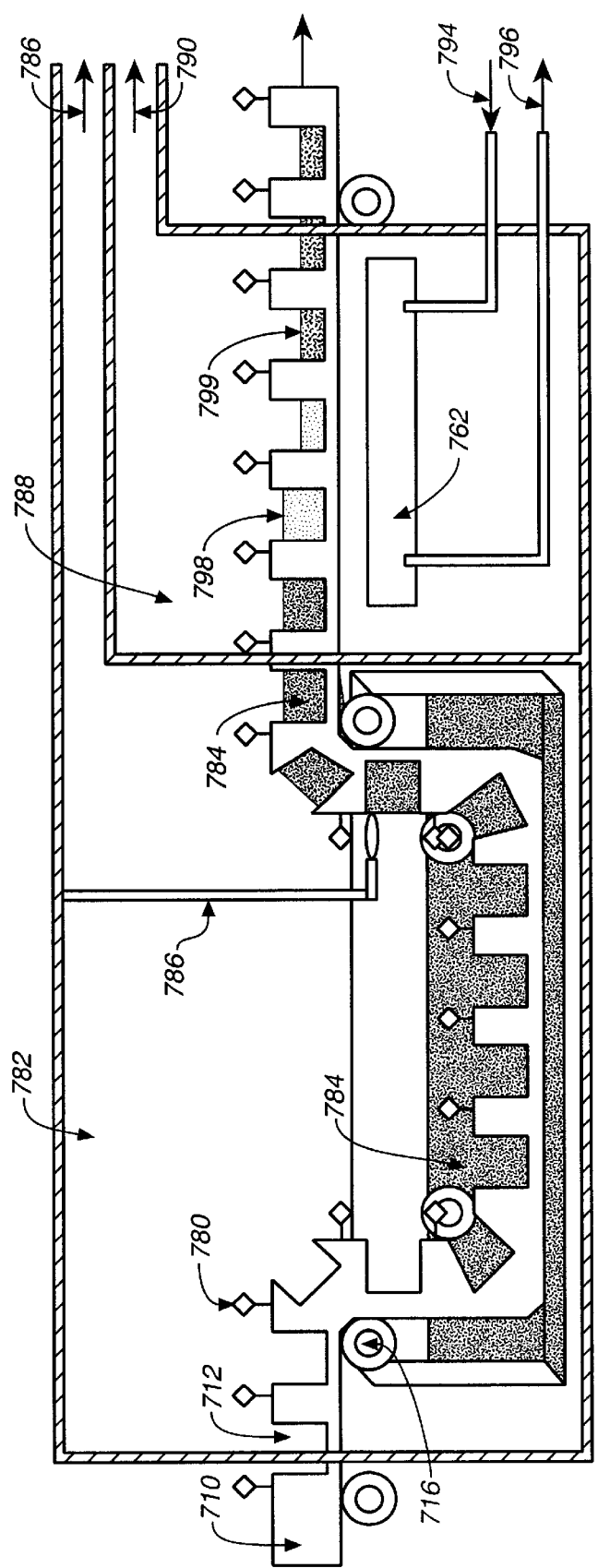
FIG._7C

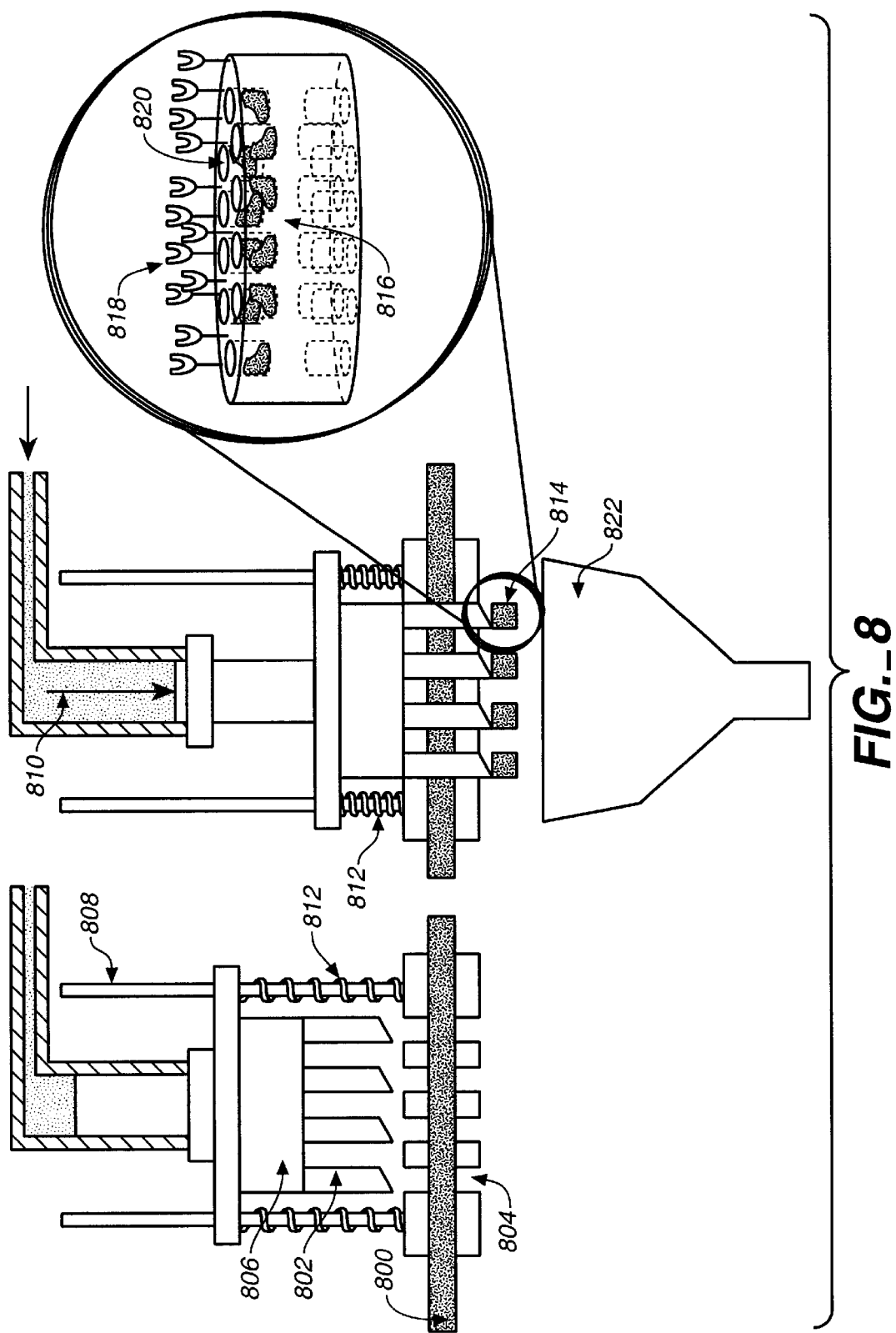
FIG._8

US 6,355,270 B1

PARTICLES FOR ORAL DELIVERY OF PEPTIDES AND PROTEINS

RELATED APPLICATIONS

This application claims the benefit of prior U.S. Provisional Application Ser. Nos. 60/115,420; 60/115,424; all filed Jan. 11, 1999.

FIELD OF THE INVENTION

The present invention relates to microfabricated devices, and more particularly to microstructural particles for use in improving the bioavailability of protein, peptide and other pharmacologically active biopolymers delivered by the oral route.

BACKGROUND OF THE INVENTION

Peptide- and protein-based therapeutic agents exhibit poor bioavailability after oral administration. This is due to poor absorption of such macromolecules across the mucosal surfaces of the stomach, intestine and colon. Moreover, peptidase enzymes found in abundance in the gastrointestinal (GI) tract destroy many peptide and protein drug before they have an opportunity to be absorbed. A variety of delivery systems have been devised to improve the oral bioavailability of drugs including, enterically-coated tablets (including osmotic pumps), capsules, and particles, liposomes, micro- and nanoparticles composed of biodegradable polymers such lactide-co-glycolides, microemulsions with surface active agents incorporated, biodegradable hydrogels, and the like. In many instances, the dosage forms incorporate penetration enhancers (also known as carriers). These agents include bile salts (as sodium salt such as sodium glycocholate), anionic detergents (such as docusate sodium and sodium lauryl sulfate), nonionic detergents (medium chain triglycerides, propylene glycol), salicylates, acyl amino acids, and acylcarnitine. Other enhancers are known to increase intestinal permeability through action on the tight junctions. An example of this type of agent is zonula occludens toxin (ZOT).

SUMMARY OF THE INVENTION

The invention includes, in one aspect, a particle for use in oral delivery of a biopolymeric drug such as a polypeptide, protein or polynucleic acid to a subject. The particle has a substrate having front and back faces, and defining at least one reservoir which opens to said front face. A biopolymer agent is contained in said at least one reservoir in releasable form. A muco-adhesive agent is carried on the substrate's front face, for attaching the particle to the intestinal mucosal lining, so that drug released from the reservoir is presented directly to the region of intestinal lining at which the particle is attached.

The particle is preferably disc-shaped, has a diameter in the range of 100 $\mu m^2$ to 1 mm, and a particle density of 1.00±0.05 gm/cm$^3$.

Exemplary bio-polymeric agent include factor VII, erythropoietin, human growth hormone, various colony stimulating factors, such as GM-CSF, interferons, interleukins, vasopressin, growth hormone releasing factor, relaxin, somatostatin, antibodies, insulin, atrial naturetic factor, glucagon; desmopressin, calcotonin, various angiogenic growth factors, such as VEGF, LHRH analogs, peptide antigens, vaccines, and antisense oligonucleotides and oligonucleotide analogs. The muco-adhesive agent may be plant lectin, such as wheat germ agglutinin, tomato lectin, *Ulex europaeus* agglutinins I and II, *Phaseolus vulgaris* agglutinin, asparagus pea lectin (*Lotus tetragonologus*), *Mycoplasma gallisepticum* lectin, B-subunit of cholera toxin (CT), *Escherichia coli* type-1 fimbriae, vitamin $B_{12}$, riboflavin, folate, or iron/transferrin, that binds to the intestinal mucosa. The agent may be mixed with an excipient to achieve a controlled rate of dissolution and release of the agent from the reservoir. One of the reservoirs may contain a permeation enhancer, and one may contain a peptidase inhibitor.

In another aspect, the invention includes a composition of the drug-delivery particles. The composition preferably contains an enteric-coating material that encapsulates the particles and which is effective, after oral delivery, to remain intact while passing through the low pH environment of the esophagus and stomach, and to dissolve in the higher pH environment of the intestinal lumen, releasing said particles.

In still another aspect the invention includes a microfabrication method for producing a the drug-delivery particles. The method generally includes the steps of (a) exposing a sheet of particle-forming material to a photoablating light source through a photomask, thereby forming a reticular lattice pattern on the sheet corresponding to the desired particle size and shape, and continuing this exposing until the desired particles are formed.

These are other objects and features of the invention will become apparent when the following detailed description of the invention is read in conjunction with the accompanying figures.

BRIEF DESCRIPTION OF THE DRAWINGS

FIGS. 1A–1E illustrate typical micro-particles of the present invention. Each is made of a substrate material (100) and contains blind pores or reservoirs such as 102 in FIGS. 1A–1D and 104 in FIG. 1E. Possible shapes include disc-like (FIG. 1A), cup-like (FIG. 1B), hexagonal (FIG. 1C) and ring-like (FIG. 1D).

FIG. 2 shows the use of enteric-coated capsule (204), the preferred means of transporting a suspension of particles (202) of the present invention through the stomach (206), with release in the small intestine (210).

FIG. 3 illustrates drug-filled particles (302) binding via ligands (306) chemically grafted the particle face (304) to receptors expressed (309) on the mucin layer (308) which overlays the intestinal epithelium (310). Each pore of the particle (312) contains a dry mixture of the biopolymeric drug to be delivered plus excipients (including permeation enhancers and/or peptidase inhibitors). The dry agent is hydrated and solvated by the influx of water (314) and moves outwardly, by diffusion (316) passing through the intestinal epithelium (either pericellularly or transcellularly) and enters the hepatic portal circulation (314).

FIG. 4 shown the sequence of step in the top-down fabrication of micro-particles using a combination of vapor or thin film deposition followed by photolithography.

FIGS. 5A–5C illustrate the structural features of micro-particles made from trak-etched polycarbonate or polyester sheets. Each particle (504) contains multiple uniform, cylindrical, blind pores (502). A layer of reactive chemical groups such as primary amino groups (510) may be introduced onto the face of the particles and mucoadhesive ligands (512) grafted via these groups to the particle face. A drug/excipient solution is filled into the pores (514) and dried (FIG. 5D).

FIG. 6 shows an example of one the reaction sequence that can be used to graft protein ligands, such as plant lectins, onto the face of the particles. Surface amino groups are reacted with a heterobifunctional reagent such as SMCC to introduce thiol-reactive maleimide groups. Thiolated lectins such as wheat germ agglutinin or tomato lectin are then reacted with the thiol-reactive groups to create thiol-ether linkages between the maleimide and thiols on the proteins.

FIGS. 7A–7B illustrates the key steps in the continuous process of creating microparticles out of polymer sheetstock. Details of the process are given in Example B, below. Briefly, the process begins with rolls of polycarbonate sheets obtained commercially that contain 150–200 micron diameter cylindrical pores on both faces, a backing material applied to the back face and a thin layer of reactive amino groups introduced onto the front face. The material is unrolled, and sheets advanced on a mechanized belt equipped with roll-guides. The first step, to convert the surface amino groups into thiol-reactive groups, is shown in the first module (FIG. 7A). While advancing through the second module (FIG. 7B), a ligand is chemically grafted to the face of the polycarbonate. Drug/excipient solution (with or without permeation enhancer and/or peptidase inhibitor) is filled into the pores and dried in the third module (FIG. 7C).

FIG. 8 illustrates the "punching" of individual microparticles from the polycarbonate sheets, the final step of the process described in FIG. 7 above. The apparatus used is similar to a hole-punch. The polycarbonate sheet (800) advances under an array of cylindrical rods (802), the diameter of which corresponds to the desired diameter of the microparticles. As the rod array moves downwards into an array of receiving openings (804), driven be a pneumatic piston (810), the rods punch individual microparticles (814) out of the sheet which are collected in the collecting funnel (822).

DETAILED DESCRIPTION OF THE INVENTION

I. Definitions

Unless Indicated Otherwise, the Terms Below have the Following Meaning.

"Particles" or "microparticles" or "microfabricated structures" or "microfabricated particles" are particles formed by microfabrication methods.

"Microdevices" or "microfabricated devices" are particles that have been additional prepared to include biological agents as coatings and/or therapeutic agents.

"Microfabrication methods" refer methods employing photomasking or patterned beam irradiation of a substrate to produce desired surface pattern features in the substrate. Exemplary microfabrication methods include photolithography, x-ray lithography and electron-beam lithography.

"Microfocal transmucosal transport" refers to the movement of intact bioactive peptide, protein, or other macromolecular therapeutic agents from the lumen of the gastrointestinal tract (either pericellularly or transcellularly) through a microscopic area of the mucosal surface (about $4 \times 10^4 \mu m^2$) and into the hepatic portal circulation.

"Mucoadhesive" refers to the capacity of particles to adhere to the mucosal layer which lines the entire surface if the small and large intestine. Adherence is mediated by ligands grafted to the one surface of the particles which bind to chemical receptors present in mucin or the surface of the intestinal epithelial cells.

"Bioerodible" refers to a material that is dissolvable in physiological medium (e.g., an erodible metal), or a biocompatible polymeric material that can be degraded under physiological conditions by physiological enzymes and/or chemical conditions, e.g., conditions found in the GI tract.

The term "molecular coating" is used herein to describe a coating which is bound to one surface (face) of a particle. The molecular coating is bound directly to the surface of the particle or grafted to the surface via a chemical bond to an electron donating group, e.g. —$NH_2$, OH or the like derivatized onto or associated with the surface of a structural layer of the particle. In a preferred embodiment, the molecular coating is limited to the face of the particle to which the reservoirs or pores-empty. Molecular coatings that confer the ability for the particle to bind to the mucin layer covering the small and large intestine (mucoadhesive ligands) are preferred.

A. Microfabricated Particles

The present invention provides microfabricated particles that are useful therapeutically in a variety of in vitro, in vivo and ex vivo applications, in particular, oral applications. The microfabricated particles have a selected nonspherical shape, uniform dimensions and contain a therapeutic agent in releasable form. The activity of the agent is expressed following its release from the device (which is designed to adhere to the mucosal surfaces of the intestine and/or colon) and transport of then agent through the gastric mucosa into the hepatic portal circulation.

The shape, size, density, and composition of the microfabricated particle of the present invention are selected to favor the adhesive force (provided by the mucoadhesive agent grafted to face of the particle). Opposing this force are to forces which would tend to dislodge the particles once they have bound to the intestinal surface (i.e., the flow of liquefied material through the intestinal lumen as a consequence of the peristaltic motion of the gut).

The number and volume of reservoirs or pores in each particle is selected to provide adequate carrying capacity for the particular biopolymer to be delivered and further to provide capacity to carry adequate amounts of appropriate permeation enhancers and/or peptidase inhibitors. For example, devices designed to be used in typical oral applications are preferably substantially disk-shaped, cup-shaped, ring-shaped, or hexagonal-shaped. Exemplary embodiments of such disk-, cup-, ring- or hexagonal-shaped devices are illustrated in FIGS. 1A–1D. In reference to FIGS. 1A–1E, each particle is composed of substrate 100 and contains one or multiple pores or reservoirs 102.

FIG. 1E shows a disk-shaped particle composed of a thin disk material 104 with diameter D between about 100–5000 microns and a thickness between about 10 microns and about 100 microns. The disk is formed of a single polymer material which may contain the therapeutic agent (e.g., a therapeutic biopolymer) within pores or reservoirs 106. Although non-erodible, biocompatible materials may be used, the preferred particles are formed of bioerodible materials, as described below.

The face of the particle containing the openings to the reservoirs or pores may be modified by the introduction of a 50–100 Å layer of reactive chemical groups. Typically these groups are added after formation of the particles. Methods of derivatizing a variety of glass, metal surface and polymer surfaces are well known. For example, amino or thiol groups can be grafted to the surface of polymers using glow discharge or "plasma" treatment.

Particles of the present invention are made muco-adhesive by chemically linking muco-adhesive ligands to the reactive groups on the face of the particle. Protein ligands are linked to amino- and thiol-reactive groups under conditions effective to form thioether or amide bonds respectively. The ligands illustrated are intended for binding the particle to selected target sites in the GI tract, e.g., the small or large bowel. Methods for attaching antibody or other polymer binding agents to an inorganic or polymeric support are detailed, for example, in Taylor, R., Ed., *PROTEIN IMMOBILIZATION FUNDAMENTALS AND APPLICATIONS*, pp. 109110 (1991).

The minimum dimensions of the particles are constrained only by the microfabrication process itself and the carrying capacity of each particle. As is described more fully below, it is recognized that "traditional" photolithography is limited to the microfabrication of structures greater than about 0.5 microns, but that substantially smaller structures (with dimensions contemplated in the present invention—e.g., 50–200 (nm diameter devices) may be produced using known X-ray and/or electron beam lithography. methods.

The optimal dimensions, shape and density of the substrate material of particles of the present invention depend on a striking a favorable balance between the dynamic movement of fluid in the gut propelled by peristaltic contractions of the smooth muscle surrounding the entire GI tract and the capacity of the particles to adhere to the mucin layer. The maximum dimension of the devices (the diameter of the disk in the case of disk-shaped devices) is typically in the range between 100 (should consider as small as 10 microns) and 1000 microns.

One key advantage to using particles that are more than a few microns in diameter is that particles of this size are too large to be endocytosed by intestinal epithelial cells. Particles that are endocytosed have at least two disadvantages. First, the therapeutic payload may be deactivated as it is processed by the endothelial cell before it reaches the desired target site. Second, the potential toxicity of the particulate carrier is of greater concern if it is endocytosed than if it is cleared through the GI tract.

Certain layers and coating which may be contained in a device such as described above (e.g., a layer of mucoadhesive ligands) can be as thin as a single layer of molecules. The minimum size again depends on the application. For example, in the case of devices made from biodegradable materials, the smaller the device, the faster it will dissolve. The stability of device of the present invention in a particular application may be readily determined by one of skill in the art using tagged (e.g., fluorescent or radiolabeled) devices in a model system.

Another important property of particles is the bioerodibility of the material employed in making the particle. Some metals, such as iron, are rapidly dissolved in aqueous media, whereas others, such as gold, are much more slowly eroded. Therefore, to achieve a desired rate of erosion, metals may be mixed in alloy.

A variety of bioerodible polymers, including polyglycolic, polylactic, polyurethane, celluloses, and derivatized celluloses may be selected, and a variety of charged polymers, such as heparin-like polysulfated or polycarboxylated polymers are suitable in forming one or more of the microstructure layers.

Further, the particles can be tagged so as to allow detection or visualization. For example, microdevices are rendered radioactive by implantation or surface attachment of radioactive isotopes such as I-123, I-125, I-131, In-111, Ga-67 and Tc-99m. Radioactive devices bound to particular regions of the GI tract can be identified by a radiation detectors such as the (-ray cameras currently used in scintigraphy (bone scans), resulting in identification and localization of such regions. Microdevices can also be tagged with fluorescent molecules or dyes, such that a concentration of microdevices can be detected visually.

The structural material used in forming the microstructure is selected to achieve desired erodibility and drug release properties. In the case of drug release, the structural material may be a one or more biodegradable polymer. Classes of biodegradable polymers include polyorthoesters, polyanhydrides, polyamides, polyalkylcyanoacrylates, polyphosphazenes, and polyesters. Exemplary biodegradable polymers are described, for example, in U.S. Pat. Nos. 4,933,185, 4,888,176, and 5,010,167. Specific examples of such biodegradable polymer materials include, for example, poly(lactic acid), polyglycolic acid, polycaprolactone, polyhydroxybutyrate, poly(N-palmitoyl-trans-4-hydroxy-L-proline ester) and poly(DTH carbonate).

To facilitate tracking of a therapeutic particle of the present invention, one of the structural or coating elements of the particle may be designed to be detectable using, for example, X-radiation, scintigraphy, nuclear magnetic resonance, optical inspection (e.g., color, fluorescence), or ultrasound.

B. Oral Delivery Composition

For oral delivery, the particles are typically delivered in an oral delivery composition made up of a plurality of the particles in a selected releasable form. The composition can be made by mixing the particles with suitable non-aqueous carriers (such as oil or micronized powder) and filled in unit dose amounts into standard enteric-coated capsules or, alternatively, compressed into tablets and coated with an enteric coating material. The enteric coating insures that the particles are transported in dry form through the low (acidic) pH environment of the stomach and released at pre-selected regions of the small or large intestine.

FIG. 2A shows typical particles of the present 202 invention filled into standard enteric-coated capsule 204. As illustrated in FIG. 2B, the enteric-coated "carrier" is designed to carry the dry particles through the low pH environment of the stomach 206 and release the particles within the higher pH environment found in the lumen of the large and small intestine 208. The particles bind via the mucoadhesive ligand grafted on the face to the mucosal lining of the GI tract 210.

The composition may be coated with a protective polymer. This material is applied by film coating technology to either tablets or capsules to protect the product from the effects of, or prevent release of drugs in, the gastric environment. Such coatings are those which remain intact in the stomach, but will dissolve and release the contents of the dosage form once it reaches the small intestine. The purpose of an enteric coating is to delay release of drugs which are inactivated by the stomach contents. In addition, release of the drug will occur in the region best suited to maximize the bioavailability of the drug.

One of the most extensively used enteric polymer is cellulose acetate phthalate (CAP). Another useful polymer is polyvinyl acetate phthalate (PVAP) which is less permeable to moisture, more stable to hydrolysis and able to ionize at a lower pH than is CAP. These properties allow more reliable release of the drug in the duodenum. Another example of currently used polymers is those based on methacrylic acid-methacrylic acid ester copolymers with acid ionizable groups. Represented among these are polymers having the tradename Eudragit available through Rohm Pharma. Generally, the enteric coating will be applied from about 0.5% by weight to about 10% by weight of the tablet or capsule. All these polymers are capable of protecting the drug in the stomach while allowing rapid and complete release of the drug containing particles from a tablet or capsule in the duodenum.

In addition to the outer protective enteric coating, the chambers in which drug and other excipients are located on the particles can also contain a protective cover or layer of material. This material can be a water-soluble substance such as cellulosic derivative like hydroxypropyl methylcellulose or gelatin. Alternatively, a less water-soluble polymer such as methylcellulose could be used to delay release of the drug from the chambers following release of the particles in the duodenum.

"ChronSet®" technology developed by ALZA Corporation (Mt. View, Calif.) can be used to release a bolus of the particles at designated times and at targeted absorption sites after passage from the stomach into the small intestine. In this case, a suspension of particles is loaded into ChronSet capsules. After swallowing, the capsules pass intact through the stomach. He shell is engineered to regulate the rate of water imbibition the osmotically permeable portion of the system. The osmotic engine expands to push and separate two halves of the capsule. The length of the capsule halves is specifically designed to produce separation at pre-selected times. The contents of each capsule are expelled into the intestinal lumen at 2 to 20 hours after administration. Greater than 80% of contents (in this case a suspension of drug-filled micofabricated particles) is expelled within 15 minutes time frame. This approach provides a means of releasing the suspension of the particles at preselected areas of the small or large intestine. In the case of the present invention, such a system may be used to release the biopolymer-containing particles at sites in the small or large intestine that are optimal for binding (i.e., areas which contain receptors for the muco-adhesive ligand grafted to the particles) and/or absorption (i.e., regions of the intestinal epithelium that are sensitive to on-board permeation enhancers).

C. Drug-Delivery Features

FIG. 3 shows a disk-shaped particle 302 having pores opening to the face of a particle 304, and a layer of muco-adhesive ligands grafted to the face 306. The particles are shown after release from an enteric-coated carrier. They are bound to a mucin layer 308 of the GI tract via receptors present in the mucin layer 309 which coats the intestinal epithelium 310. In the embodiment shown in FIG. 3A, the pores are filled with a dry mixture of a therapeutic agent and an excipient designed to delay the dissolution of the mixture for 5 to 60 minutes after the particle is released from the enteric capsule within the lumen of the small or large intestine 312. Suitable muco-adhesive ligands are listed in Table 1 below.

As shown in FIG. 3B, as water in the GI tract solvates the dry drug/excipient mixture 314, the therapeutic agent 316 is released from the pores, penetrates the epithelium 310 and enters the hepatic portal circulation 318. Other embodiments may contain an erodible plug to delay the release of the therapeutic agent. The pores of the particle may be plugged with a material, such as a corrosion delay film. The corrosion delay layer is typically made of a material that gradually dissolves in the biochemical environment of the GI tract. Examples of such plug materials include thin layers of metals such as titanium, gold, silver, platinum, copper, and alloys and oxides thereof, gelatin, polysaccharides such as maltodextrins, enzyme-sensitive materials such as peptide polymers. The thickness of the corrosion delay layer may be selected to, for example, provide the desired delay of release within the GI tract, to allow the device to bind to its target before therapeutic agent is released. These layers may be applied by standard metal deposition procedures, sputtering, thin film deposition (see Wagner, *J Oral Implantol* 18(3): 231–5;1992.

FIG. 5C illustrates a general embodiment of a particle containing a grafted layer of reactive mucoadhesive ligands 512. The particle contains pores or reservoirs 514 each of which is filled with a mixture of therapeutic peptide/protein and an excipient (or blend of excipients) which are selected to delay dissolution of the mixture (indicated by the stippled pattern within the pores). In one general embodiment, the mucoadhesive ligand is a mucin-binding agent, typically a lectin, polymer or antibody of antibody fragment, for binding the particle to the intestinal mucosa. As illustrated in FIG. 5D, the therapeutic peptide/protein solution is dried after filling into the reservoirs (as indicated by the retracted stippled pattern within each reservoir.

The activity of the therapeutic agent is expressed by exposure of the particle to the aqueous environment of the small or large intestine. The target site can be a particular location in bowel. For example, in the case where the target is a particular segment of the small intestine, the ligand and rate of release may be tailored to insure binding to such a site and release of the drug at the site.

The therapeutic agent contained in the therapeutic particles of the present invention is releasable. A releasable agent is a therapeutic compound, such as a drug, that is designed to be released from the reservoirs of the particle while the particle is bound to the intestinal mucosa. Exemplary peptide and oligonucleotide therapeutic agents for use in the invention include those given in Table 3.

An important feature of the invention is the capacity to include permeation enhancers 'on-board' each particle, formulated either as a mixture with the agent or in separate chambers or compartments of individual particles, which are released in conjunction with the agent. Limiting enhancer exposure of the intestinal mucosa to the circumscribed microscopic region between the orifice-side of each bound device and the juxtaposed mucosal surface has two important advantages. Firstly, focally high concentrations of the enhancer are achieved in the same region as the agent. It is well known that permeation enhancement is strongly influenced by the local concentration of both the enhancer and agent. Secondly, the vast majority of the mucosal surface is not exposed to the potentially irritating affects of high concentrations of the enhancer. Suitable enhancers include bile salts, non-ionic surfactants, anionic surfactants, lecithins, medium chain glycerides and fatty acids, salicylates, sodium 3-nitrobenzoate, acylcarnitines, acylcholines, acyl amino acids, calcium chelators, and peptides capable of loosening the tight junctions between epithelial cells such as Zot (See Table 2).

A preferred enhancer for use with the present invention is Zonula occludens toxin (Zot). Zot is a novel toxin elaborated by Vibrio cholerae that modulates intestinal tight junctions. For example, Zot reversibly increases rabbit intestinal permeability to insulin by 72% (P=0.034) and immunoglobulins by 52% (P=0.04) in vitro. When tested in vivo, Zot induced a 10-fold increase of insulin absorption in both the rabbit jejunum and ileum, whereas no substantial changes were detected in the colon. Similar results were obtained with immunoglobulins, whereby Zot induced twofold and six-fold increases of IgG absorption in the jejunum and ileum, respectively. In diabetic rats, bioavailability of oral insulin co-administered with Zot was sufficient to lower serum glucose concentrations to levels comparable to those obtained after parenteral injection of the hormone. The survival time of diabetic animals chronically treated with oral insulin+Zot was comparable to that observed in parenterally treated rats (Fasano, et al, *J Clin Invest.* 99:1158–64;1997 and Fasano, et al. *Gastroenterology* 112:839–46;1997). The putative receptor in the jejunum and ileum is GM1(Walia et al, *Infect Immun* 67:5215–5222;1999). Further evidence that that Zot acts by opening tight junction between intestinal epithelial cells has been reported by Fasano, et al (*J Clin Invest* 6(2):710–20;1995).

A further advantage provided by microfabrication is the capacity to include inhibitors of proteolytic enzymes 'on-board' each device, formulated either as a mixture with the agent or the enhancer, or in separate compartments of individual particles. Release of enzyme inhibitors in conjunction with the agent and in the same circumscribed region between the orifice-side of the device and the mucosal surface is advantageous, since high concentrations of the inhibitor are achieved in this region optimizing the protective effect of the inhibitors.

After binding to the mucosa, drug is released from individual particles in high concentrations within the circumscribed volume trapped between the surface of the bound particle and the juxtaposed mucosal surface, thus driving 'microfocal' transmucosal transport of such agents. Drug release is delayed from several minutes to one hour after the particles are released from the enteric capsule into the intestinal lumen. This delay period is designed to insure that the particles have an opportunity to bind to the mucosal surface. Release is delayed by one of two approaches described below:

In one approach, prior to filling of the reservoirs, a solution of the drug is mixed with a solution of a water-soluble excipient. The mixture is then dried within the reservoirs. The excipient is selected to delay re-hydration and dissolution of the mixture after release of the dry particles from the enteric capsule and exposure to water within the intestinal lumen. Suitable excipients are listed in Table 4.

A second general release approach employs an erodable plug material placed above the dried drug solution within the pores. Such material can be dissolved or suspended in an oil or non-aqueous solvent and filled above the dried drug solution, plugging the opening of the reservoir. Suitable materials are listed in Table 4.

In addition to poor intrinsic transport, peptide and protein drugs are susceptible to degradation by peptidase enzymes that are present in abundance within the intestinal lumen. A variety of peptidase inhibitors have been identified. The particles of the present invention can also contain on-board protease inhibitors to further improve the bioavailability of peptide and protein drugs. These agents include, among others, aprotinin, ($_1$-antiyrypsin), and EDTA. These agents act to preserve the integrity of peptide and protein drugs within the intestinal tract. Such enzyme inhibitors may be filled, by the same approached used for the permeation enhancers described above, into biopolymer filled particles of the present invention. Such "on-board" enzyme inhibitors are released in conjunction with the drug, preserving their integrity while in the intestinal lumen and thus promoting trans-epithelial transport.

D. Microfabrication Methods

"Top-down" fabrication of micro-devices, using techniques perfected by the electronics industry, provides the means to create microscopic particles with a unique combination of structural features useful for the present invention. Such particles can be made with extremely precise sizes and shapes and can contain pores, which, for the purposes of the present invention, act as reservoirs enabling the particle to transport therapeutic biopolymers. Moreover, the particles may be asymmetrical. For example, the pores or reservoirs can be made to open only to the top face of the particle. The top face (containing the pore openings) can also be chemically modified to contain reactive chemical groups such as primary amino or thiol groups, which can be used to chemically graft protein or other types of ligands to this face only. As will become evident in the discussions below, the unique geometry provided by such microfabrication methods is useful to create the particles of the present invention.

Two microfabrication schemes may be employed to create the particles of the present invention. The first is the so called "top-down" approach which employs a combination of thin film deposition methods plus photolithography, photoablation and etching techniques to deposit and mold sequential layers of materials on a substrate. Using this approach, materials such as $SiO_2$ and polymers are applied as a thin film to a sacrificial layer by standard techniques including chemical vapor deposition, sputtering or the like. Subsequent layers of materials may be added, including photoresist materials which, when exposed to the proper wavelength of UV light or other source of irradiation, either undergo a chemical change which renders the resist layer susceptible to the action of etchants (positive resist) or resistant to the action of etchants (negative resist). Photomasks are used to expose only selected areas of such resists to the source of irradiation and etchants are used to dissolve susceptible areas.

A second general microfabrication scheme employed in the present invention is based on track-etch methodology. In this case, polymer films are exposed to high-energy particles in a nuclear reactor. These high-energy particle penetrate the film to a depth of 10–30 $\mu$m (depending on the source and power of the energy level of the particle), leaving sensitized tracks in the polymer. The tracks are then etched with strong alkaline solutions creating uniform-sized, cylindrical-shaped, blind pores in the polymer sheet. This approach is used create sheet-stock of polymers such as polycarbonate or polyester with uniform pores etched into both faces. For the purposes of the present invention, a thin layer of non-porous backing can be applied to one face, creating an asymmetrical film with pores opening to only the front face. The pores act as reservoirs for biopolymer drugs, which are filled into the pores by submersion of the film into a solution of the drug under reduced pressure. The drug solution is then dried and individual particles are cut from the polymer sheet stock using a microfabricated punch apparatus.

In one general embodiment, the particles are microfabricated from a material designed to erode in the GI tract. As examples, the particles may be formed of metals such as iron, titanium, gold, silver, platinum, copper, and alloys and oxides thereof. Preferably for this invention the particles may be formed of a biodegradable polymer material.

The structural portion or substrate layer (i.e., microstructure) of the particles of the present invention may be microfabricated using any suitable microfabrication method, such as track-etching (PCTE) of polymer roll stock detailed in Example B, or the photolithography and photoablation methods detailed below. It will be appreciated that the particles can also be microfabricated using other microfabrication methods known to those skilled in the art, such as x-ray or electron beam lithography. Electron beam lithography has been used to produce sub-micron circuit paths (e.g., Ballantyne, et al., *J. Vac. Sci. Technol.* 10:1094 (1973)), and may be used (e.g., in combination with near field scanning microscopy) to generate and image patterns on the nanometer scale (see, e.g., INTRODUCTION TO MICROLITHOGRAPHY, Thompson, et al., Eds., ACS Symposium Series, Washington D.C. (1983)).

FIGS. 4A–4H illustrate the steps in forming a disk-shaped reservoir-containing particle 400 (FIG. 4E) by photolithographic techniques. As shown, the structure includes a polymer layer forming a planar expanse 402. This polymer expanse is formed according to conventional methods for deposition of metal layers, e.g., chemical vapor deposition, sputtering or the like, and/or methods for producing thin polymer sheet material.

As a first step in the process, the polymer layer is attached or otherwise bonded to a sacrificial layer 404, such as phosphorous doped silicon dioxide which is in turn coated onto a standard silicon wafer 406. The top of the polymer layer is coated with a photoresist layer 408 by chemical vapor deposition. Suitable negative- or positive-resist material are well known, e.g., INTRODUCTION TO MICROLITHOGRAPHY, Thompson, et al., Eds, ACS Symposium Series, Washington D.C (1983). Additional details on microfabrication methods useful in the manufacture of devices according to the present invention are described in, e.g., co-owned PCT patent publications WO 95/24261, WO 95/24472 and WO 95/24736.

The coated polymer layer is irradiated through a photomask 410 having a series of circular openings, such as opening 412, corresponding in size to the desired size of the particles. Methods for forming photomasks having desired photomask patterns are well known.

In the embodiment described with reference to FIGS. 4A–4D, the photoresist is a negative resist, meaning that exposure of the resist to a selected wavelength, e.g., UV, light produces a chemical change (indicated by cross hatching) that renders that altered resist resistant to etching by a suitable etchant. The appearance of the coated polymer layer after photomask irradiation UV FIG. 3C. As seen, the polymer layer 402 is now covered by a plurality of discrete disk-shaped resist elements, such as elements 408, corresponding in size to the planar dimensions of the desired particles.

The polymer layer is now treated with an etchant material effective to dissolve the polymer in the exposed areas of the polymer layer. In the case of a metal layer, the etchant may be a suitable acid solution; in the case of a laminate biodegradable polymer layer, the etchant could be an enzyme solution, an aqueous solution having a pH effective to break down the polymer, or an organic solvent known to dissolve the particular polymer. The polymer layer, after complete etching, has the appearance of FIG. 4C, which shows a series of disk-like, resist-coated elements on the sacrificial layer. In the final preparation steps, the resist is removed by suitable chemical treatment (FIG. 4D).

FIGS. 4E–4H illustrate further photolithographic processing effective to produce disc-shaped particles containing pores or reservoirs, such as shown at 400. In this processing, the etched polymer/sacrificial layer structure or substrate shown in FIG. 4D is further coated with a positive resist material 414, as shown in FIG. 4E. The coated polymer is then irradiated through a second photomask 416 having a series of circular openings, such as opening 418, whose diameters correspond to the desired "internal" diameters of the reservoirs. The mask is aligned with the substrate, as shown, so that the mask openings are in registry with the already formed discs in the substrate.

Irradiation of the substrate through the photomask causes photo-induced changes in the resist (indicated by cross-dot pattern) that renders the irradiated regions susceptible to a selected etchant. The appearance of the coated laminate after photomask irradiation UV is shown in FIG. 4F. As seen, the polymer layer 402 is now covered by a plurality of discrete disk-shaped positive resist elements, such as elements 420, corresponding in size to the planar dimensions of the desired reservoirs. The polymer layer is now treated with a suitable second etchant material. The timing of the etching step is selected so that the layer is etched only partially creating blind pores in the layer. The appearance of the polymer after such etching is shown in FIG. 4G. As seen, this treatment has produced cylindrical pores, such as opening 430, in the center of each microstructure 400 in the substrate. Removal of the sacrificial layer produces the free particles 400 shown in FIG. 4H.

It will be appreciated that the particles formed as just described may be further treated by standard photolithographic techniques to produce other desired surface features and or layers. Further, reservoirs or pores may be filled with a material different from the microstructure material by known methods. For example, such reservoir may be filled with a selected therapeutic protein, such as interferon, insulin, various proteases, lutenizing releasing hormone and its analogs, and the like.

In another general approach, the particles are patterned from a substrate by excimer laser photoablation techniques. Methods of laser micromachining or dry etching have been described, e.g., U.S. Pat. Nos. 5,368,430, 4,994,639, 5,018, 164, 4,478,677, 5,236,551, and 5,313,043. This method is most suited to a polymeric substrate, because of the ease with which a laser beam cans photoablate polymer structures.

Particles of the present invention such as 504 illustrated in FIG. 5A, may also be made by cutting or 'punching' individual particles from a variety of polymeric sheet-stock containing track-etched pores. Such polymeric sheet-stock made of polycarbonate and polyester is commercially available. The pores are uniform, cylindrical, blind pockets or reservoirs on both faces such as pores 502 in FIG. 5A. A non-porous backing material 128 may be added to one face of the sheet, creating an asymmetric structure in which the pores open to only one face. Reactive chemical groups such as amino functions 510 in FIG. 5B may be introduced onto the face of the sheet to which the pores open.

II. Applications

Particles and compositions of the present invention can be administered to a subject in need of therapeutic intervention via the oral route. As discussed above, particles of the present invention are particularly useful in the delivery of poorly absorbed protein, peptide, oligonucleotide and other biopolymeric drugs.

III. Examples

A. Microfabricated Particles for Oral Deliver of EPO

FIGS. 4A–4H illustrate the steps in forming a disk-shaped particle by photolithographic techniques on a standard 4" type single crystal (SC) silicon wafer. 100 nm of silicon oxide is thermally grown on the SC silicon substrate at 1000° C. under "wet" conditions to form an etch-stop layer (not shown). A sacrificial layer of poly-crystalline silicon (poly; 1830 nm) is deposited on the etch-stop layer by low pressure chemical vapor deposition (LP-CVD) in a Tylan furnace (605° C., 300 mTorr, 100.0 sccm $SiH_4$) and the wafer is annealed for 1 hour at 1000° C. to remove residual stresses. A 900 nm layer of LTO is deposited on the sacrificial poly by LP-CVD in a Tylan furnace (450° C., 300 mTorr, 60.0 sccm $SiH_4$, 90.0 sccm $O_2$, 0.4 sccm $PH_3$) to form the microparticle layer, and again the wafer is annealed for 1 hour at 1000° C. to density the LTO. The wafers are patterned on the LTO surface by UV photolithography GCA 6200 DSW Wafer Stepper (GCA MANN Products) to yield a photo-resist (PR) pattern of circular-shaped areas about 100–200 microns on diameter. The wafer is then baked. The exposed areas of the LTO on the PR patterned LTO surface are etched in a LAM plasma etcher (850W @ 0.38 cm gap, 2.8 Torr, 120.0 sccm He, 30.0 sccm $CHF_3$, 90.0 sccm $CF_4$). Remaining photoresist is removed in pirhana (5 parts 18M $H_2SO_4$, 1 part 30% $H_2O_2$) to yield a wafer having separate microparticles attached to an underlying poly layer.

The remaining LTO particles are coated with a second, positive, resist layer, exposed to UV light for a second time through a photomask with a finer pattern of circular openings. The diameter of the opening and the density of the opening within the .photomask are selected to provide suitable pores or reservoirs of 10–20 microns in diameter in the LTO particles. The exposed layer is then treated with a second etchant material effective to partially dissolve the polymer in the exposed areas creating a plurality of cylindrical- or cone-shaped pores or reservoirs in each particle. Importantly, conditions are adjusted so the sheet is etched to a desired depth, but not completely through the polymer layer. In the case of a metal layer, the etchant may be a suitable acid solution; in the case of a biodegradable or biocompatible polymer layer, the etchant could be an enzyme solution, an aqueous solution having a pH effective to break down the polymer, or an organic solvent known to dissolve the particular polymer.

Next, the upper surface of the particles is chemically modified to produce reactive chemical groups such as primary amino or thiol, groups. A preferred method of introducing such groups into the first few molecular layers of polymer material is gas plasma treatment described in detail for polycarbonate roll-stock below.

The sacrificial poly layer is then removed by a wet etch in 6M KOH at 80° C. (1–2 minutes) to release the particles into solution. After the particles are released the pH is promptly reduced to below 8 and the particles are stored in neutral H20 (resistivity >17.8 Mohms/cm). The particles are suspended in PBS and muco-adhesive ligands are grafted to the particle face via these reactive chemical groups using the same methods as those described below.

The therapeutic peptide or protein solution is filled into the pores at this point in the process. The particles are thoroughly washed in distilled water, collected on a filter and dried under reduced pressure. The particles are resuspended in a degassed solution of EPO plus excipients as described in detail in Example B below. The suspension is subjected to reduced pressure to insure that trapped air is forced from the pores in the particles. The are fully immersed in the solution and the pressure is elevated slightly above atmospheric to insure that the solution enters all the pores. The particles are once again trapped on a filter and dried using one of the three methods described in detail below (Example B)

B. Polycarbonate Roll-stock with PCTE Micro-reservoirs for Oral Delivery of EPO

Roll-stock of 50–75 $\mu$m thick polycarbonate track-etch (PCTE) polymer sheet material is obtained from commercial sources such as Osmonics Laboratory and Specialty Products Group (111 Lindbergh Avenue, Livermore, Calif. 94550). The specified pore density is $1-5\times10^5$ pores/cm$^2$, the pore diameter is 10–20 $\mu$m and the pore depth is 12–25 $\mu$m.

PCTE is manufactured in a two step process. In the first, the 50–75 $\mu$m thick polycarbonate film is exposed to collimated high-energy particles ((40 mev) emanating from a plutonium source. These particles penetrate about 12–25 $\mu$m into both sides of the film and leave sensitized tracks along their path. The number of tracks per cm$^2$ depends on the amount of time the film is in the reactor. In this case the time is adjusted to create a pore density of about $1-5\times10^5$ pores per cm$^2$. In the second step, the tracks left by the particles are preferentially etched into uniform, blind cylindrical pores or reservoirs by exposure to strong alkaline solution such as NaOH. The temperature, strength (molarity) of the etching solution and time are adjusted to create pores of approximately 10–20 $\mu$m in diameter and 12–25 $\mu$m deep. A laminate backing may be applied to one side of the polycarbonate sheets.

Grafting of Primary Amine Groups to Face of Polycarbonate Sheets

A Glow Discharge or Gas Plasma technique is used to introduce reactive primary amino groups into the face of the polycarbonate sheets (roll-stock). Gas Plasma Surface Modification is done in a vacuum chamber in the presence of ammonia vapor and has been used to modify plastics and polymer surfaces (Kany et al, *Biomaterials* 18(16):1099–107;1997 and Siphia, *Biomater Artif Cells Artif Organs* 18(3)37–46; 1990 and Benedict and Williams, *Biomater Med Devices Artif Oragns* 7(4):477–93; 1979 and Liu, et al, *J Biomed Mater Sci* 27(7):909–15;1993. An air-to-air reel-to-reel continuous film-processing machine may be utilized to maximize efficiencies. Such processing equipment is available on a contract basis at MetroLine, Inc. (251 Corporate Terrace Corona, Calif. 91719). Processing rates up to fifteen feet per second can be achieved and greatly reduce the cost of processing. Wire tubing up to six parallel lines, or films up to 24 inches wide are easily accommodated.

Gas plasma is ionized gas, the fourth state of matter. A plasma is formed when a gas, in this case ammonia, is exposed to energy, generally an electric field. Cold gas plasma reactions are conducted in a vacuum chamber, built of either Pyrex, quartz or aluminum, and having either an internal or an external electrode configuration. Low-pressure gases are then ionized using a radio frequency (RF) power, at 13.56 MHz. The RF energy strips electrons from the gas species, producing free electrons, ions and excited molecules. As the active molecules recombine with the electrons, photons are released, causing the "glow" which is associated with gas plasmas. Each gas type "glows" with a specific color. As soon as the RF power is turned off, the gas molecules recombine to form stable molecules, and are evacuated from the chamber.

Gas plasma surface modifications used here falls into the categories of molecular modifications (often referred to as 'etching' or molecular modification of a surface) will result in a new chemical surface without actually depositing any additional materials.

There are a number of critical parameters which are controlled during the plasma treatment cycle. Any change in these parameters will influence the outcome of the modification. They include: gas type power, pressure, flow, and sure time C. Chamber and Fixture Configuration Various other factors may effect treatment, such as ambient conditions, relative humidity during component molding, surface contamination of the substrates, or polymer lot-to-lot variations. A molecular modification alters the chemical structure of the surface of an organic material, in this case polycarbonate. Ammonia gas also ionizes under the influence of the electrical discharge. Molecules traveling at high speeds during the ionization cycle impact with the surface of the polycarbonate causing the polycarbonate polymer backbone to fracture and form reactive species such as radicals. Some of the ionized ammonia molecules then attach themselves to the substrate surface, thus forming a layer of covalently bound primary amino groups.

Ammonia plasma discharge modification generally involves from 25 to 250 angstroms of the substrate surface and thus does not alter the bulk properties of the underlying polymer substrate.

Reactive amine groups can also be introduced into polymer surfaces using glow discharge techniques in the presence of alkylamine vapors such as butylamine (Tseng and Edelman, *J Biomed Mater Res* 42(2):188–98;1998) and ethylene-diamine (Denizli et al, *J Biomater Sci Polym Ed* 10(3):305–18;1999).

Radiofrequency glow discharge treatment in the presence of water or $H_2O_2$ vapor, or glow discharge in air ($O_2$) may also be used to introduce reactive hydroxyl groups into polymer surfaces (Patterson, et al, ASAIO 41(3):M625–9;1995 and Kang et al, *Biomaterials* 17(8):841–7;1996 and Vargo et al, *J Biomed Mater Res* 29(6):767–78;1995 and Ozden et al, *Dent Mater* 13(3):174–8;1997). Water-soluble condensing agents such as carbodiiamide are used to link amino-containing protein ligands to the —OH-modified polymer surface. Polycarbonate can be modified by introduction of reactive double bonds by treatment with glycidyl acrylate (Karmath and Park, *J Appl Biomater* 5(2):163–73;1994).

It should be noted that other surface modification techniques such as graft polymerization by h-irradiation may be used to introduce reactive groups to the face of the particles (see for example, Ikadal, *Biomaterials* 15(10):725–36;1994 and Amiji and Park, *J Biomater Sci Polym Ed* 4(3):217–34;1993 and Kamath and Park, *J Appl Biomater* 5(2):163–73;1994).

D. Chemical Coupling of Lectins to Amino-Modified Polycarbonate Surface

FIG. 7 illustrates the system for the continuous fabrication of particles of the present invention. In reference to FIG. 7A, the polycarbonate roll-stock 710 with 10–20 µm diameter pores or reservoirs 712 and surface reactive amino groups 714 (obtained commercially from Osmonics/MetroLine, see above) is advanced on a belt equipped with roller guides such as 716. The sheet advances to trough 718 and is submerged in a solution of SMCC or similar heterobifunctional reagent 720 (Pierce Chemical Company, Rockford, Ill. 61105), introducing thiol-reactive maleimide groups onto the face of the polycarbonate 712.

The reaction is virtually stoichiometric (FIG. 6). Heterobifunctional reagents with extended spacer arms also be used to improve coupling efficiencies by reducing steric hindrance (Bieniarz et al, *Bioconjugate Chem* 7:88–95; 1996). As the sheet moves out of the trough, some solution remains in the pores 724. The sheet then passes into vacuum chamber 726. When the vacuum is applied, water vapor moves out of the chamber 728 and is condensed (not shown). Pressure within vacuum chamber 726 may be alternately reduced and then raised to insure that any trapped air is cleared from the pores. Within the vacuum chamber, the sheet is rinsed by spaying the sheet from nozzle 730 with water 732, which is collected in drainage area 734 and removed by drain 736. The sheet next advances into vacuum chamber 738. A high vacuum is applied and water remaining within the pores 740 evaporates and water vapor passes out of the chamber 742. The pores are now dry 744. The sheet containing the thiol-reactive maleimide groups advances 746 to the ligand modification module (FIG. 7B).

With reference to FIG. 7B, the polycarbonate roll-stock 710 with 10–20 □m diameter pores or reservoirs 712 and thiol-reactive maleimide surface groups 748 introduced above is placed in a reel-to-reel configuration so that as the polycarbonate sheet advances on a belt, roller guides such as 716 cause it to dip into trough 750. Within the trough, the sheet is submerged in a solution highly purified wheat germ agglutinin or Lycopersicon esculentum (tomato) lectin 752. Either lectin is obtained as a lyophilized powder from Sigma Chemical Company (St. Louis, Mo. 63178). A solution of twenty milligrams of each powder is made in 1 mL of phosphate-buffered isotonic saline (PBS).

Prior to placement in the trough, either lectin is thiolated using SPDP following the procedure of Carlsson et al (*Biochem. J* 173:723–37;1978). Conditions are adjusted to yield 1.5–6 —SH groups per lectin molecule after mild reduction. The thiolated lectin is chemically linked to the thiol-reactive maleimide groups 754 (FIG. 6). The speed of the advancing roll and the temperature are adjusted to insure adequate coupling of the thiol-containing lectin to the thio-reactive polymer as the polymer film passes through the trough. The movement of the polycarbonate sheet may be halted to accommodate sufficient time for lectin coupling to the submerged segment. As the sheet moves out of the trough, some solution remains in the pores 756.

The polycarbonate sheet is then washed either by passage through a second trough containing distilled water (not shown) or sprayed with distilled water. In the case of spray washing, the sheet passes into vacuum chamber 758. When the vacuum is applied, water vapor moves out of the chamber 760 and is condensed (not shown). With in the vacuum chamber, the sheet is rinsed by spaying the sheet from nozzle 762 with water 764, which is collected in drainage area 766 and removed by drain 768. After washing, the sheet next advances into vacuum chamber 770. Within this chamber, the film is gently dried to insure that the pores are emptied of any fluid. In the case of freeze drying, a flat heat exchanger is placed in good thermal contact (directly below) the polycarbonate film. Liquid refrigerant at temperatures ranging from −20° C. to −60° C. (such as Freon or a cold liquid such as liquid nitrogen) is passed through the heat exchanger in order to freeze any water remaining on the film or within the pores. The pressure is reduced until all the water sublimes.

In the example shown in FIG. 7B, drying is achieved by evaporation of the remaining water under reduced pressure in vacuum chamber 770, or by passage of a stream of warm air or an inert gas such as nitrogen over the surface of the film (not shown), or by freeze drying as mentioned above. In the case of vacuum drying exemplified here, a high vacuum is applied and water remaining within the pores 772 evaporates and water vapor passes out of the chamber 774. The pores are now dry 776. The sheet containing the lectin chemically grafted to the surface advances 778 to the filling module (FIG. 7C).

E. Filling Reservoirs with EPO; Mixing EPO with Excipients which Provide Delayed Release from Micro-reservoirs A solution of 50 mg/mL human recombinant erythropoietin (EPO, 80,000 units per milligram, Sigma Chemical Company) is made in PBS. A range of water-soluble excipients can be added to this solution to delay dissolution when dried. These include polymers, dextrans, maltodextrins, gelatins, disintegrants such as Explotab, polyplasdone, amberlite IRP 88, maize or potato starch and Elcema P100.

F. Filling Reservoirs with EPO/Excipient Solution

In reference to FIG. 7C, polycarbonate roll-stock 710 with pores 712 and chemically grafted lectin groups 780 introduced above is passed along a belt equipped with roller guides such as 716. A degassed solution of EPO/excipients 784 is placed in a trough in a sealed chamber 782. Segments of the polycarbonate roll stock (which has been modified with the wheat germ agglutinin, tomato lectin or other suitable muco-adhesive agent) are advanced on rollers into the chamber and submerged in the trough. To remove any trapped air within the reservoirs in the submerged segments of the polycarbonate film, the pressure within the chamber is reduced 786, and then raised slightly above atmospheric pressure. This procedure is repeated as new segments of the roll stock advance through the trough. As the film leaves the trough, a rubber blade 786 scrapes off any excess EPO solution and returns it to the trough. Alternatively, a rapid stream of forced air (or inert gas such as nitrogen) is generated across the surface of the film as it leaves the filling trough, forcing any excess EPO solution into a collecting duct, returning it to the filling trough (not shown).

G. Mixing EPO/Excipient Solution with Permeation Enhancers and/or Peptidase Inhibitors EPO is a relatively large polypeptide and, as such, its intrinsic absorption potential by the mucosa of the large and small intestine is minimal and thus oral bioavailability is poor. For this reason it is necessary to incorporate permeation enhancers and/or peptidase inhibitors 'on-board' the delivery particle to be released in conjunction with the EPO. Both such enhancers and enzymes inhibitors are known to improve peptide and protein absorption in a dose dependent manner.

In this case, suitable water-soluble permeation enhancers and/or peptidase inhibitors are mixed with the EPO/excipient solution and filled into the reservoirs in the polycarbonate film as described above. Release of enhancer and/or peptidase inhibitors from the reservoirs in conjunction with the drug facilitate movement of the EPO across the intestinal epithilium in vivo.

H. Drying

After filling of EPO/excipient solution (plus or minus permeation enhancer and/or peptidase inhibitor solution) into the reservoirs of the tomato lectin- or wheat germ agglutinin-modified polycarbonate film, drying is achieved by one (or a combination) of three methods. Water is removed by evaporation under reduced pressure in a vacuum chamber,788, or by passage of a stream of warm air or an inert gas such as nitrogen over the surface of the film (not shown), or by freeze frying. In the case of freeze drying, a flat heat exchanger 792 is placed in good thermal contact (directly below) the polycarbonate film. Refrigerant fluid at temperatures ranging from –20° C. to –60° C. (such as Freon or a cold liquid such as liquid nitrogen) is passed through the heat exchanger flowing into port 794 and passing out port 796 in order to freeze any water remaining on the film or within the pores 798. The pressure is reduced until all the water sublimes 799.

I. Creation of Microscopic Discs from Polycarbonate Sheet Stock Using Micromachined 'Disc-punch' Apparatus 1. Microfabrication of "disc-punch" Apparatus FIG. 8 is a diagram of a micromachined "disc-punch" apparatus designed to function much like a microscopic paper hole-punch. The drug-filled polycarbonate film is advanced into the apparatus along roll guides and aligned beneath a two-dimensional array of protruding cylindrical rods of 100 m–1 mm in diameter and about 10–100 mm in length. Below the sheet is an array of cylindrical holes, the openings of each designed to receive a single rod as it is lowered. The receiving openings are fabricated to fit the rods as tightly as possible and are open on the bottom. Below the holes is a collection funnel.

2. Continuous Punching of 200 μm EPO-filled Discs from Polycarbonate Sheet Stock To function, the polycarbonate sheet 800 containing pores filled with EPO is advanced into the punch assemble and the rod array 802 is lowered into the openings of the receiving array 804 in one swift downward motion using a press 806 fitted with guide rods 808 to insure precision alignment. The system is preferably equipped with a pneumonic piston 808 to provide the downward motion during pressurization 810 and a set of resisting springs 812 to retract the rod assembly upwardly as the piston is de-pressurized (illustrated in FIG. 8). The down-up movement of the rods punches disc-shaped particles out of the polycarbonate sheet 814. The insert illustrates an individual particle 816 with ligand attached to the face and pores filled with dry EPO/excipient mixture. After the rod assembly retracts, the particles, which fall from the open bottom of the openings, are collected using the receiving funnel 822. Since the particles are dry and small, the sides of the funnel may be vibrated to facilitate movement of the particles down the funnel into a collecting vessel. Alternatively, a stream of air may be used to propel the particles out of the openings, down the funnel and into the receiving vessel. The process is made continuous by advancing the polycarbonate sheet while the down-up motion of the rod array is repeated.

3. Filling Drug-filled Particles into Enteric-coated Capsule and Administration

The dry, EPO-filled particles collected above are weighed, mixed with appropriate filler powder (such as micronized lactose or microcrystalline cellulosesugar), divided into appropriate unit doses and filled into standard enteric-coated capsules. The oral route is used to administer the capsules to patients suffering from anemia at appropriate doses and schedules.

TABLE 1

Muco-adhesive Ligands

| Ligand | Binding Specificity |
|---|---|
| Plant lectins | |
| Wheat germ agglutinin | (D-glcNAc)$_2$ |
| Tomato lectin | (D-glcNAc)$_4$ |
| *Ulex europaeus* agglutinin I and II | (-L-fucose |
| *Ulex europaeus* agglutinin II | (D-glcNAc)$_2$ |
| *Phaseolus vulgaris* agglutinin | Galactose/NAcGal |
| *Lotus tetragonologus* (Asparagus pea lectin | (-L-fucose |
| Vitamins | |
| Vitamin B$_{12}$ | Respective receptor |
| Riboflavin | Respective receptor |
| Folate | Respective receptor |
| transferrin | Respective receptor |
| Polymeric materials | |
| tragacanth | |
| Carbopols (polycarbophil) | |
| polyacrylic acid and related substances | mucin/cell surface glycoproteins |
| sodium carboxymethylcellulose | (non-specific binding) |
| polyethylene oxide | |
| poly(methyl vinylether co-maleic anhydride | |
| sodium alginate | |
| methyl cellulose | |
| poly(acrylic) acid and polycarbophil | |
| Bacterial/viral invasion factors | |
| *Escherichia coli* type-1 fimbriae | galactoproteins/gangliosides |
| *Mycoplasma gallisepticum* lectin | sialic acid |
| B-subunit of cholera toxin | gangliosides |

TABLE 2

Preferred Penetration Enhancers

| Class of Enhancer | Specific Examples |
|---|---|
| Bile Salts | Glyo-deoxycholate |
| | Taruro-dexoycholate |
| | Tauro-chenodeoxycholate |
| | Glyco-chenodexycholate |
| | Taurocholate |
| | Glycocholate |
| | Glycoursocholate |
| | Tauroursocholate |
| | Dexoycholate |
| | Chenodeoxycholate |
| | Cholate |
| | Ursocholate |
| Non-ionic Surfactants | Polyoxyethylene (POE) ethers (e.g., Brij, Texaphor) |
| | Alkylphenoxy-POEs (Triton, Igepal, Surfonic) |
| Anionic Surfactants | sodium dodecyl sulfate |
| | dioctyl sodium sulfosuccinate |
| Lecithins | Lysolecithin |
| Medium chain glycerides | mono-, di-, or triglycerides of C8, C10, or C12 fatty acids |
| Medium chain fatty acids | sodium caprylate |
| | sodium caprate |
| | sodium laurate |
| Salicylates | sodium salicylate |
| Acylcarnitines | decylcarnitine |
| | laurylcarnitine |
| | myristoylcarnitine |
| Acylcholines | Laurylcholine |
| | Palmitoylcholine |
| Acyl amino acids | N-laurylphenylglycine |
| | N-palmitoylglycine |
| Calcium chelators | Ethylenediaminetetraacetic acid (EDTA) |
| Peptides | PZ-peptide |
| | Zonula occludens toxin (ZOT) |

TABLE 3

Injectable Pharmacologically Active Bio-polymers

| Agent | Disease or Condition |
|---|---|
| Erythropoietin | anemia |
| human growth hormone | Dwarfism, short stature |
| granulocyte colony stimulating factor | Chemotherapy-induced neutropenia |
| Interferon (αβγτ) | Hepatitis |
| interleukins | Cancer |
| vasopressin | Diabetes insipidus |
| growth hormone releasing hormone | Dwarfism, short stature |
| relaxin | Systemic and diffuse scleroderma |
| somatostatin | Acromegaly |
| antibodies to tumor necrosis factor | Inflammation |
| insulin | Diabetes |
| atrial natruretic factor | Sodium imbalance |
| glucagon | Hypoglycemia |
| desmopressin | Diabetes insipidus, hemophilia A |
| calcitonin | Osteoporosis |
| Oligonucleotides (antisense) | Cancer, infectious diseases, inflammatory diseases |
| LHRH analogs (leuprolide, nafarelin, goserelin, deslorelin, historelin, buserelin and the like) | Prostate cancer |

TABLE 4

Excipients and Plug Materials for Use in Delayed Release of Bio-polymer

| Material | Mechanism of Erosion |
|---|---|
| Gelatin | Solubilization by water |
| Polyethylene glycol | Solubilization by water |
| Fatty acids and triglycerides | Solubilization by heat |
| Polyvinyl pyrrolidone | Solubilization by water |
| Starch | " |
| Cellulose ethers (eg., HPMC) | " |
| Hydrocolloidal gums and mucilages (e.g., gum arabic, guar gum, gum tragacanth) | " |
| Waxes (e.g., carnuba, bees) | Solubilization by heat |
| Polyacrylic acid derivatives and esters | Solubilization by water and pH |
| shellac | Solubilization by pH |
| Cellulose acetate phthalate | " |
| Carboxy methylcellulose | Solubilization by water |

These and other objects and features of the invention will become more fully apparent when the following detailed description is read in conjunction with the accompanying drawings.

It is claimed:

1. A particle for use in oral delivery of a biopolymeric drug such as a polypeptide, protein or polynucleic acid to a subject, comprising
   a substrate having front and back faces, and defining at least one reservoir which opens to said front face,
   a biopolymer agent contained in said at least one reservoir in releasable form, and
   a muco-adhesive agent carried on said front face, for attaching the particle to the intestinal mucosal lining, wherein drug released from the reservoir is presented directly to the region of intestinal lining at which the particle is attached.

2. The particle of claim 1, wherein the bio-polymeric agent is selected from the group consisting of GM-CSF, interferons, interleukins, vasopressin, growth hormone releasing factor, relaxin, somatostatin, antibodies, insulin, atrial naturetic factor, glucagon, desmopressin, calcotonin, various angiogenic growth factors, such as VEGF, LHRH analogs, peptide antigens, vaccines, and antisense oligonucleotides and oligonucleotide.

3. A particle of claim 1, wherein the muco-adhesive agent is a plant lectin that binds to the intestinal mucosa.

4. The particle of claim 3, wherein muco-adhesive agent is selected from the group consisting of wheat germ agglutinin, tomato lectin, *Ulex europaeus* agglutinins I and II, *Phaseolus vulgaris* agglutinin, asparagus pea lectin (*Lotus tetragonologus*), *Mycoplasma gallisepticum* lectin, B-subunit of cholera toxin (CT), *Escherichia coli* type-1 fimbriae, vitamin $B_{12}$, riboflavin, folate, or iron/transferrin.

5. The particle of claim 1, having a disc-like shape, a diameter in the range of 100 $\mu m^2$ to 1 mm and a particle density of 1.00±0.05 gm/$cm^3$.

6. The particle of claim 1, wherein at least one reservoir contains a permeation enhancer.

7. The particle of claim 6, wherein the biopolymer and permeation enhancer are contained in separate reservoirs.

8. The particle of claim 1, wherein at least one reservoir contains a peptidase inhibitor.

9. The particle of claim 1, wherein the reservoir containing the biopolymeric agent also contains an excipient designed to delay dissolution/release of the agent from the reservoir.

10. The particle of claim 9, wherein the excepitent is selected from the group consisting of gelatin, polyethylene glycol, fatty acids and triglycerides, polyvinyl pyrrolidone, starch, cellulose ethers (eg., HPMC), hydrocolloidal gums and mucilages (e.g., gum arabic, guar gum, gum tragacanth), waxes (e.g., carnuba, bees, polyacrylic acid derivatives and esters, shellac, cellulose acetate, phthalate or carboxy methylcellulose.

11. The particle claim 1, wherein the substrate is formed of polycarbonate or polyester.

12. The particle of claim 1, which further includes a non-porous laminate backing at attached on the back face of the particle.

13. An oral delivery composition, comprising a plurality of drug-deliver particles of claim 1.

14. The composition of claim 13, which further includes an enteric-coating material that encapsulates said particles and which is effective, after oral delivery, to reamin intact while passing through the low pH environment of the esophagus and stomach, and to dissolve in the higher pH environment of the intestinal lumen, releasing said particles.

15. The composition of claim 14, wherein the enteric-coating material is effective to dissolve at a pH in the range of 6.0–6.8.

16. The composition of claim 14, wherein the enteric-coating material is Eudragit L100 or S100.

17. The composition of claim 14, wherein the enteric-coating material is a Chronset system with preselected release time.

18. The composition of claim 17, wherein the Chronset system is designed to release the particle suspension in the middle regions of the small intestine.

19. A microfabrication method for producing a plurality of particles of claim 1, comprising exposing a sheet of particle-forming material to a photoablating light source through a photomask, by said exposing, forming a reticular lattice pattern on said sheet corresponding to the desired particle size and shape, and continuing said exposure until the desired particle are formed.

20. The method of claim 19, wherein one face of said sheet, corresponding to said particle front face, is grafted with a layer of reactive amino or thiol groups by plasma (glow) discharge.

21. The method of claim 20, which further includes linking muco-adhesive ligands to said one sheet face.

* * * * *

UNITED STATES PATENT AND TRADEMARK OFFICE
CERTIFICATE OF CORRECTION

PATENT NO.    : 6,355,270 B1                                        Page 1 of 1
DATED         : March 12, 2002
INVENTOR(S)   : Mauro Ferrari et al.

It is certified that error appears in the above-identified patent and that said Letters Patent is hereby corrected as shown below:

<u>Title page,</u>
Item [56], OTHER PUBLICATIONS, insert:
-- John P. Ranieri, et al. "Neuronal cell attachment to fluorinated ethylene propylene films with covalently immobilized laminin oligopeptides YIGSR and IKVAV. II," Journal of Biomedical Materials Research, vol. 29 No. 6, Jun. 1995. --

<u>Column 21,</u>
Lines 11-13, claim 12 should read:
-- 12.   The particle of claim 1, which further includes a non-porous laminate backing attached on the back face of the particle. --
Lines 16-21, claim 14 should read:
-- 14.   The composition of claim 13, which further includes an enteric-coating material that encapsulates said particles and which is effective, after oral delivery, to remain intact while passing through the low pH environment of the esophagus and stomach, and to dissolve in the higher pH environment of the intestinal lumen, releasing said particles. --

Signed and Sealed this

Thirteenth Day of May, 2003

JAMES E. ROGAN
*Director of the United States Patent and Trademark Office*